(12) United States Patent
Demers et al.

(10) Patent No.: US 7,993,050 B2
(45) Date of Patent: Aug. 9, 2011

(54) TWO-STAGE MIXING SYSTEM, APPARATUS, AND METHOD

(75) Inventors: Jason A. Demers, Manchester, NH (US); Matthew C. Harris, Bow, NH (US); David W. McGill, Bedford, NH (US); Larry B. Gray, Merrinack, NH (US); Edward L. Staub, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 442 days.

(21) Appl. No.: 11/926,891

(22) Filed: Oct. 29, 2007

(65) Prior Publication Data

US 2008/0112258 A1 May 15, 2008

Related U.S. Application Data

(62) Division of application No. 10/696,818, filed on Oct. 30, 2003, now Pat. No. 7,354,190.

(51) Int. Cl.
*B01F 13/10* (2006.01)

(52) U.S. Cl. .................................................. 366/154.1

(58) Field of Classification Search ............... 366/154.1, 366/155.1, 155.2; 422/63–67
See application file for complete search history.

(56) References Cited

U.S. PATENT DOCUMENTS

| 8,183 | A | * | 6/1851 | Wright | 366/155.2 |
|---|---|---|---|---|---|
| 2,179,271 | A | * | 11/1939 | Pick | 366/325.8 |
| 2,835,481 | A | * | 5/1958 | Cox | 366/152.1 |
| 2,915,299 | A | * | 12/1959 | Woebcke | 366/98 |
| 2,917,465 | A | * | 12/1959 | Begley | 502/6 |
| 3,326,815 | A | * | 6/1967 | Werner et al. | 516/79 |
| 4,272,824 | A | * | 6/1981 | Lewinger et al. | 700/265 |
| 5,266,272 | A | * | 11/1993 | Griner et al. | 422/104 |
| 5,935,332 | A | * | 8/1999 | Caucal | 118/429 |
| 6,796,702 | B2 | * | 9/2004 | Wire et al. | 366/152.2 |
| 6,910,797 | B2 | * | 6/2005 | Falcon | 366/127 |

* cited by examiner

*Primary Examiner* — David L Sorkin
(74) *Attorney, Agent, or Firm* — Marc J. Gorayeb

(57) ABSTRACT

A two-stage mixing system, apparatus, and method produces a solution including a first substance and a second substance in a predetermined ratio by first mixing the first substance with a first liquid to produce a first solution and then mixing the first solution with the second substance to produce a second solution. Multiple batches of second solution may be produced from a single batch of first solution. Multiple batches of second solution may be produced in parallel.

18 Claims, 22 Drawing Sheets

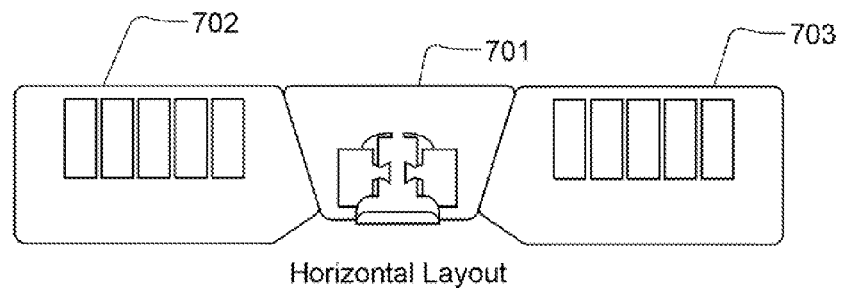
Horizontal Layout
FIG. 7A
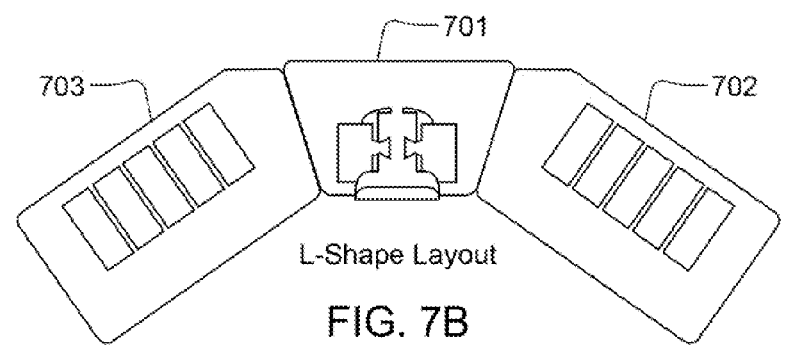
L-Shape Layout
FIG. 7B
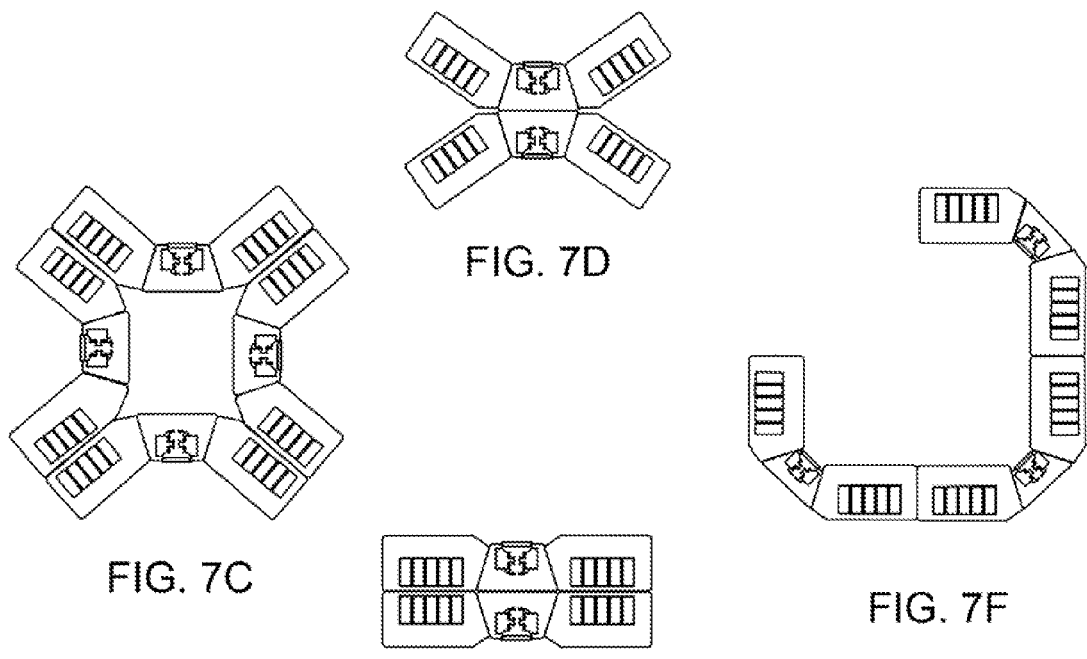
FIG. 7D
FIG. 7C
FIG. 7E
FIG. 7F

TWO-STAGE MIXING SYSTEM, APPARATUS, AND METHOD

CROSS-REFERENCE TO RELATED APPLICATION(S)

This application is a division of U.S. application Ser. No. 10/696,818 filed on Oct. 30, 2003, now U.S. Pat. No. 7,354,190, issued Apr. 8, 2008, and entitled TWO-STAGE MIXING SYSTEM, APPARATUS, AND METHOD, herein incorporated by reference.

The present application may also include subject matter related to one or more of the following commonly-owned United States patent applications or patents, each of which was filed on even date herewith and is hereby incorporated herein by reference in its entirety:

U.S. patent application Ser. No. 10/696,969, filed Oct. 30, 2003, published May 5, 2005 as U.S. Publication No. US-2005-0095576, and entitled SYSTEM, DEVICE, AND METHOD FOR MIXING A SUBSTANCE WITH A LIQUID (referred to herein as "Application D70");

U.S. patent application Ser. No. 10/696,893, filed Oct. 30, 2003, now U.S. Pat. No. 7,461,968, issued Dec. 9, 2008 and entitled SYSTEM, DEVICE, AND METHOD FOR MIXING LIQUIDS (referred to herein as "Application D71");

U.S. patent application Ser. No. 10/697,176, filed Oct. 30, 2003, published May 5, 2005 as U.S. Publication No. US-2005-0095141, and entitled SYSTEM AND METHOD FOR PUMPING FLUID USING A PUMP CASSETTE (referred to herein as "Application D73");

U.S. patent application Ser. No. 10/696,984, filed Oct. 30, 2003, published May 5, 2005 as U.S. Publication No. US-2005-0095152, and entitled DOOR LOCKING MECHANISM (referred to herein as "Application D74");

U.S. patent application Ser. No. 10/697,450, filed Oct. 30, 2003, now U.S. Pat. No. 7,632,080, issued Dec. 15, 2009 and entitled BEZEL ASSEMBLY FOR PNEUMATIC CONTROL (referred to herein as "Application D75");

U.S. patent application Ser. No. 29/192,835, filed Oct. 30, 2003 and entitled ICON FOR A PORTION OF A COMPUTER SCREEN, now abandoned (referred to hereinafter as "Application D76");

U.S. patent application Ser. No. 10/697,862, filed Oct. 30, 2003, now U.S. Pat. No. 7,662,139, issued Feb. 16, 2010 and entitled PUMP CASSETTE WITH SPIKING ASSEMBLY (referred to herein as "Application D84"); and U.S. patent application Ser. No. 10/696,990, filed Oct. 30, 2003, now U.S. Pat. No. 7,632,078, issued Dec. 15, 2009 and entitled PUMP CASSETTE BANK (referred to herein as "Application D85").

FIELD OF THE INVENTION

The present invention relates generally to pumping liquids, and more particularly to a two-stage mixing system, apparatus, and method.

BACKGROUND OF THE INVENTION

Millions of people receive blood transfusions each year. Although helpful in many cases, blood transfusions have associated risks. Among others, there is a risk that microorganisms capable of causing disease (i.e., pathogens) could pass from the donor blood to the ultimate blood recipient. For example, untreated blood used in a blood transfusion could have pathogens causing the West Nile Virus, or AIDS. It thus is critical for the public health to ensure that transfused blood is substantially free of pathogens.

The medical community has responded to this need by developing various techniques for removing known and unknown pathogens from donated blood. One technique involves mixing precise amounts of a diluted anti-pathogen compound with blood. Some time after mixing, a rinsing process removes the anti-pathogen compound from the blood. One complexity with this process, however, is the fact that the diluted anti-pathogen compound has a very short shelf life (e.g., on the order of about four hours). Accordingly, the diluted anti-pathogen compound must be produced a relatively short time before it is mixed with blood.

The anti-pathogen compound is not easy to handle before it is diluted. To the contrary, it has a very high pH (e.g., on the order of 11.0 or higher) and thus, is highly caustic and toxic. Mere contact with the undiluted solution can melt plastic, or burn flesh. Because of these undesirable properties, the undiluted solution typically is manually diluted by highly trained laboratory technicians that necessarily must be protected from direct contact with it. Consequently, laboratory technicians often are required to wear relatively impermeable protective gear while diluting the solution behind a chemical laminar flowhood. Such a process, however, is inherently slow, imprecise, and costly due to the multitude of safety requirements. Moreover, even with safeguards, diluting the undiluted solution still poses a risk to the laboratory technician.

SUMMARY OF THE INVENTION

In accordance with one aspect of the invention there is provided a two-stage mixing process to produce a solution including a first substance and a second substance in a predetermined ratio. In a first stage, the first substance is mixed with a first liquid to produce a first solution. In a second stage, the first solution is mixed with the second substance to produce a second solution. This process is particularly useful for mixing two substances that cannot be mixed directly without damaging one of the substances. The first substance is diluted sufficiently in the first solution for it to be directly mixed with the second substance without damaging either of the substances. In exemplary embodiments of the present invention, the two-stage mixing process is used in a blood processing system to produce a solution including a red blood cell concentrate (RBCC) and an anti-pathogen compound for reducing pathogens in the RBCC.

An exemplary two-stage mixing system includes a primary mixing unit for producing batches of the first solution and at least one secondary mixing unit for producing batches of the second solution. Each batch of first solution produced by the primary mixing unit may be sufficient to prepare multiple batches of second solution. Multiple secondary mixing units may operate in parallel to produce second solution from a single batch of first solution. The multiple secondary mixing units may draw the first solution from a common container.

A process controller is typically used to coordinate and control the mixing operations of the primary and secondary mixing units and the actions of the operator. The process controller may be separate from the mixing units or integrated into one of the mixing units (e.g., the process controller may be integrated into the primary mixing unit). The process controller typically includes a user interface (such as a touch screen) for interacting with the operator. Among other things, the process controller coordinates loading, priming, mixing, teardown, maintenance, and calibration functions.

In accordance with another aspect of the invention there is provided apparatus for combining a first substance with a second substance that cannot be mixed directly with the first substance without damaging at least one of the first substance and the second substance. The apparatus includes a primary mixing unit and a secondary mixing unit. The primary mixing unit mixes the first substance with a first liquid to produce a first solution. The first solution has a first predetermined concentration of first substance capable of being mixed directly with the second substance without damaging one of the first substance and the second substance. The secondary mixing unit mixes the first solution with the second substance to produce a second solution having a second predetermined concentration of first substance relative to the second substance. In an exemplary embodiment of the present invention, the first substance is an anti-pathogen compound that is mixed with a buffer solution, and the second substance is a red blood cell concentrate. Other types of diluting solutions can be used to mix with the first substance. Once mixed, the first solution typically has a limited useable lifetime, in which case the first solution is mixed with the second substance during the useable lifetime of the first solution. The apparatus may also include a process controller for controlling the primary and secondary mixing units and coordinating mixing operations of the primary and secondary mixing units. Among other things, the process controller typically monitors the quantity of first solution and prevents the secondary mixing unit from mixing the first solution with the second substance if there is an insufficient quantity of first solution for preparing the second solution. In order to produce the second solution, the process controller coordinates the primary mixing unit to produce a sufficient quantity of first solution for preparing the second solution.

In accordance with another aspect of the invention there is provided a method for combining a first substance with a second substance that cannot be mixed directly with the first substance without damaging at least one of the first substance and the second substance. The method involves mixing the first substance with a first liquid to produce a first solution so as to have a first predetermined concentration of first substance capable of being mixed directly with the second substance without damaging one of the first substance and the second substance, and mixing the first solution with the second substance to produce a second solution having a second predetermined concentration of first substance relative to the second substance. In an exemplary embodiment of the present invention, the first substance is an anti-pathogen compound that is mixed with a buffer solution, and the second substance is a red blood cell concentrate. Other types of diluting solutions can be used to mix with the first substance. Once mixed, the first solution typically has a limited useable lifetime, in which case the first solution is mixed with the second substance during the useable lifetime of the first solution. The method may also involve monitoring the quantity of first solution and preventing said mixing of the first solution with the second substance if there is an insufficient quantity of first solution for preparing the second solution. In order to produce second solution, the method may involve preparing a sufficient quantity of first solution for preparing the second solution and enabling said mixing of the first solution with the second substance when there is a sufficient quantity of first solution for preparing the second solution.

In accordance with another aspect of the invention there is provided a mixing system including a primary mixing unit for mixing a first substance with a first liquid to produce a first solution, which is stored in a container, and multiple secondary mixing units coupled to the container. Each of the secondary mixing units mixes first solution from the container with a second substance to produce a second solution having a second predetermined concentration of first substance relative to the second substance. In an exemplary embodiment of the present invention, the first substance is an anti-pathogen compound that is mixed with a buffer solution, and the second substance is a red blood cell concentrate. Other types of diluting solutions can be used to mix with the first substance. Once mixed, the first solution typically has a limited useable lifetime, in which case the first solution is mixed with the second substance during the useable lifetime of the first solution. The mixing system may include a process controller for controlling the primary and secondary mixing units and coordinating mixing operations of the primary and secondary mixing units. The process controller typically monitors the quantity of first solution and prevents the secondary mixing units from mixing the first solution with the second substance if there is an insufficient quantity of first solution for preparing the second solution. In order to produce second solutions, the process controller typically coordinates the primary mixing unit to produce a sufficient quantity of first solution for preparing the second solution by the plurality of secondary mixing units. The plurality of secondary mixing units may be coupled to the container of first solution via a single connection to the container. Each of the secondary mixing units typically requires priming with first solution prior to mixing the first solution with the second substance, in which case the process controller coordinates priming of the plurality of secondary mixing units from the container of first solution. The process controller may coordinate priming of the plurality of secondary mixing units symmetrically outward from the middle of the plurality of secondary mixing units. For example, in an embodiment having an odd number of secondary mixing units including a middle unit, the process controller typically begins priming with the middle unit and continues priming outward from the middle unit with successive pairs of units.

The mixing system may include a management rack for holding multiple second substance containers and multiple second solution receptacles for use by the secondary mixing units. The management rack typically includes a multiple compartment tray for holding the plurality of second solution receptacles. The tray is typically removable from the rack and may be stackable with other trays while holding the second solution receptacles.

In order to avoid operator confusion, the process controller typically focuses the operator on one task at a time. The process controller may control at least one visual indicator (e.g., LEDs) on each mixing unit for focusing the operator on one task at a time, and the process controller may provide a graphical display to the operator including a representation of the at least one visual indicator of at least one mixing unit. The process controller may provide a graphical display to the operator including a representation of at least one mixing unit and further including a highlighting icon for indicating any mixing unit associated with the task.

BRIEF DESCRIPTION OF THE DRAWINGS

In the accompanying drawings:

FIGS. 7A-7F show workstation tables and various workstation configurations in accordance with various embodiments of the present invention;

DETAILED DESCRIPTION OF A PREFERRED EMBODIMENT

Figure 1:
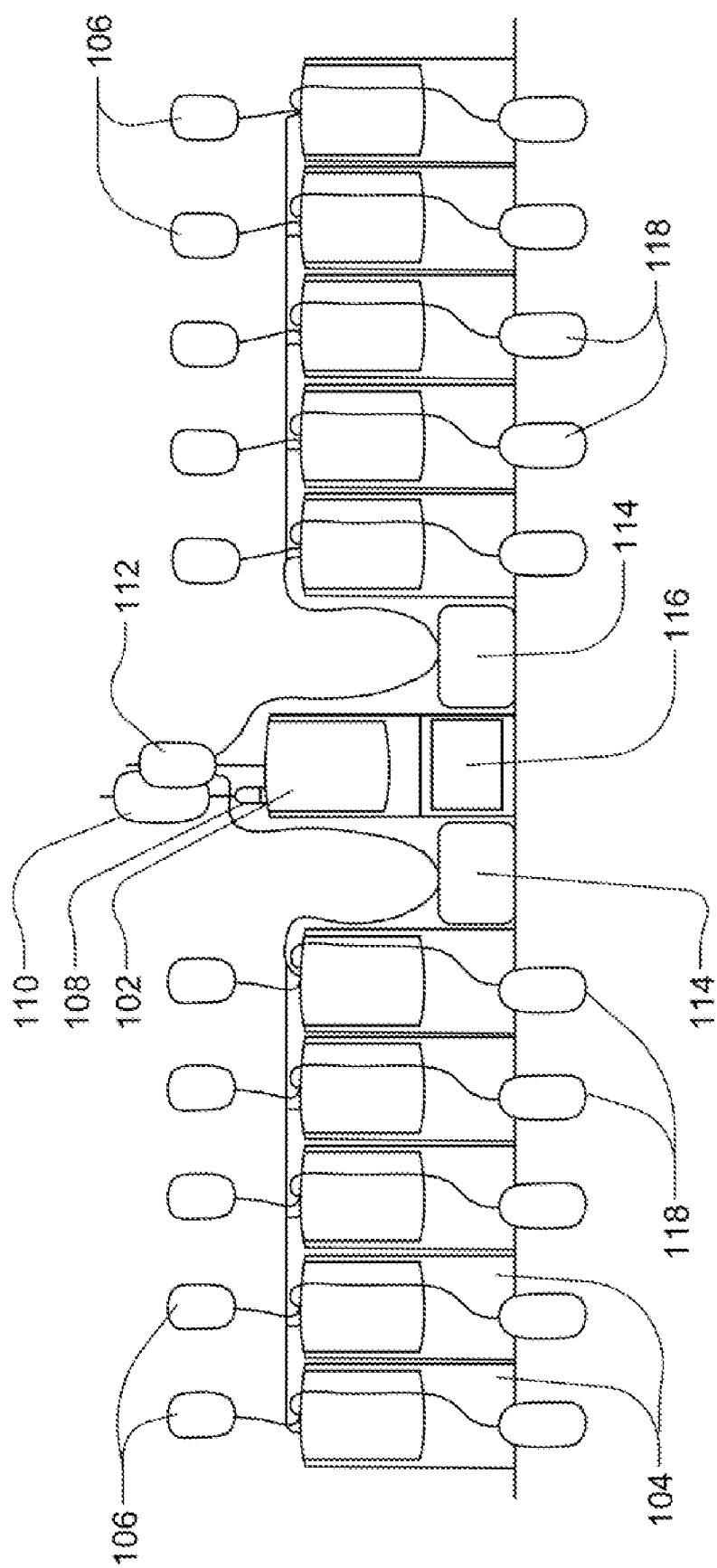
FIG. 1 shows an exemplary blood processing system in accordance with an embodiment of the present invention.

Embodiments of the present invention utilize a two-stage mixing process to produce a solution including a first substance and a second substance in a predetermined ratio. In a first stage, the first substance is mixed with a first liquid to produce a first solution. In a second stage, the first solution is mixed with the second substance to produce a second solution. This process is particularly useful for mixing two substances that cannot be mixed directly without damaging one of the substances. The first substance is diluted sufficiently in the first solution for it to be directly mixed with the second substance without damaging either of the substances.

Thus, an exemplary two-stage mixing system includes a primary mixing unit for producing batches of the first solution and at least one secondary mixing unit for producing batches of the second solution. In a typical embodiment of the present invention, each batch of first solution produced by the primary mixing unit is sufficient to prepare multiple batches of second solution. Multiple secondary mixing units may operate in parallel to produce second solution from a single batch of first solution. The multiple secondary mixing units may draw the first solution from a common container.

A process controller is typically used to coordinate and control the mixing operations of the primary and secondary mixing units and the actions of the operator. The process controller may be separate from the mixing units or integrated into one of the mixing units (e.g., the process controller may be integrated into the primary mixing unit). The process controller typically includes a user interface (such as a touch screen) for interacting with the operator. Among other things, the process controller coordinates loading, priming, mixing, teardown, maintenance, and calibration functions, as described below.

In exemplary embodiments of the present invention, the two-stage mixing process is used in a blood processing system to produce a solution including a red blood cell concentrate (RBCC) and an anti-pathogen compound for reducing pathogens in the RBCC. For convenience, this solution may be referred to hereinafter as an "incubation solution." The anti-pathogen compound is preferably a caustic anti-pathogen compound known as PEN 110™ or INACTINE™, which is an organic solvent with a pH over 11 that is distributed by V.I. Technologies, Inc. of Watertown, Mass. Because of its high pH, this anti-pathogen compound will damage the RBCC if added directly to the RBCC. Therefore, the anti-pathogen compound is first mixed with a buffer solution of sodium phosphate to a predetermined concentration (e.g., 1 part anti-pathogen compound to 99 parts buffer solution) to form an anti-pathogen working solution. For convenience, this mixing of anti-pathogen compound with buffer solution to produce working solution may be referred to hereinafter as "compounding," and an apparatus that performs such compounding may be referred to hereinafter as a "compounder" or "compounder pump." The working solution is then mixed with the RBCC to a predetermined concentration (e.g., 1 part working solution to 9 parts RBCC) to form the incubation solution. For convenience, this mixing of working solution with RBCC to produce incubation solution may be referred to hereinafter as "blood processing," and an apparatus that performs such blood processing may be referred to hereinafter as a "blood pump." The working solution has a limited useable lifetime, so blood processing is coordinated to occur within the useable lifetime of the working solution. The incubation solution is typically allowed to incubate for some period of time, after which it is rinsed to remove the anti-pathogen compound to produce a pathogen reduced blood product.

System Overview

FIG. 1 shows an exemplary blood processing system 100 in accordance with an embodiment of the present invention. Among other things, the blood processing system 100 includes a single compounder pump 102 and ten essentially identical blood pumps 104 organized as two banks of five blood pumps each. An exemplary compounder is described in Application D70. An exemplary blood pump is described in Application D71.

The compounder pump 102 pumps buffer solution from a buffer solution container 110 into a vial of anti-pathogen compound 108, and the resulting working solution is pumped into a working solution container 112. Each compounding cycle preferably produces a sufficient quantity of working solution for each of the ten blood pumps 104 to run one blood processing cycle. Each of the blood pumps 104 mixes working solution from the working solution container 112 with red blood cell concentrate (RBCC) from a RBCC container 106 to form an incubation solution that is pumped into an incubation bag 118. The blood processing system 100 typically also includes two sterile docks 114 that are used by the operator to splice together plastic tubing as necessary for various blood processing operations. The blood processing system 100 is controlled through a user interface 116.

Figure 2:
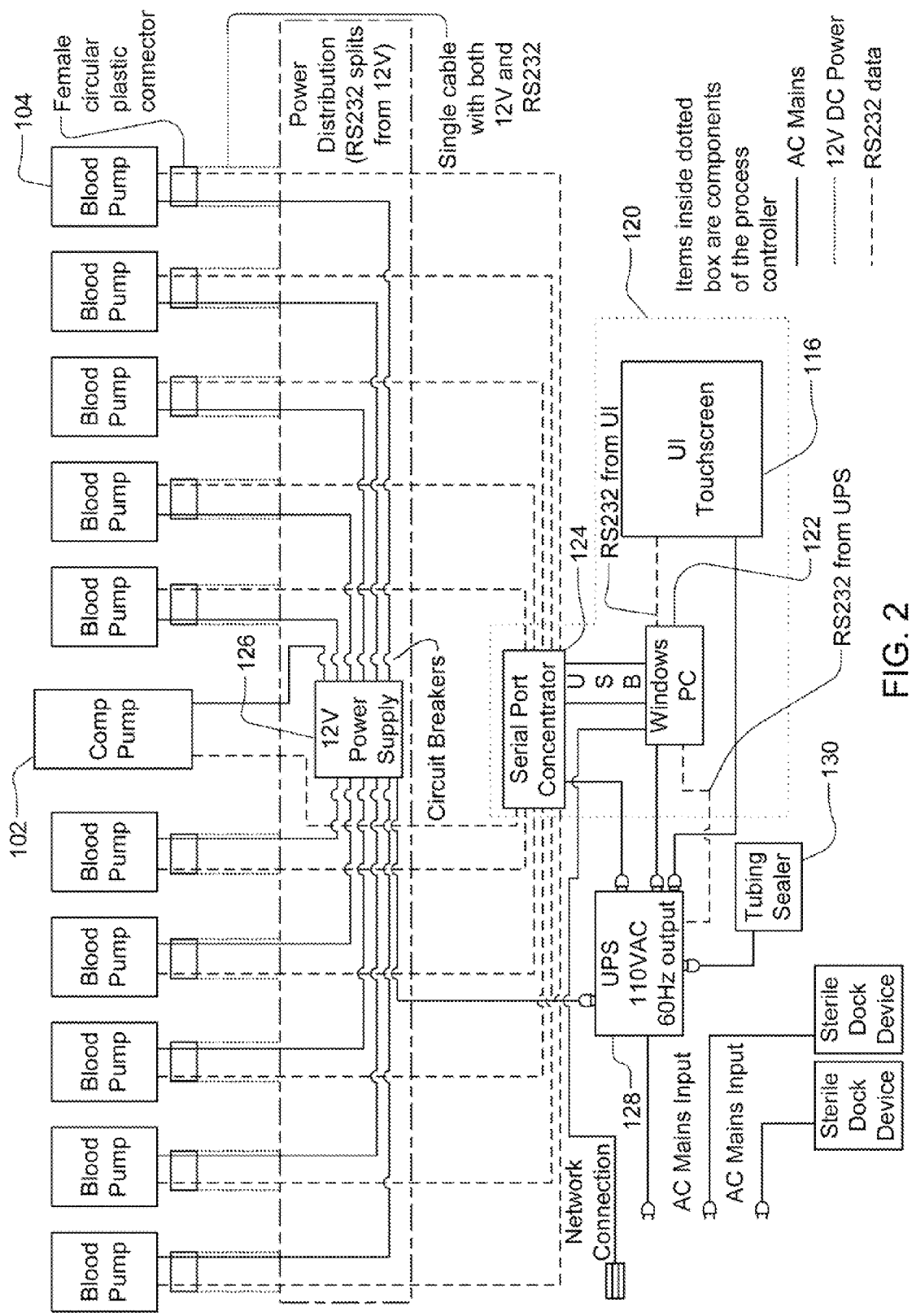
FIG. 2 shows an exemplary wiring diagram for one embodiment of the blood processing system shown in FIG. 1.

FIG. 2 shows an exemplary wiring diagram for one embodiment of the blood processing system 100. The compounder pump 102 and the blood pumps 104 are typically powered from a common 12-Volt external power supply 126, and are preferably controlled by an external process controller 120 (although the process controller functionality could also be performed by one of the pumps, such as the compounder pump 102). The process controller 120 is typically a specially-programmed Windows-based computer 122 operated through the user interface 116, and also including a serial port concentrator 124 for connecting the compounder pump 102 and blood pumps 104 to a single serial port of the computer 122, such as an RS-232 communication port. The compounder pump 102 and the blood pumps 104 are in communication with the process controller 120 through the serial port concentrator 124, for example, over RS-232 communication links. The blood processing system 100 typically includes a tubing sealer 130 for sealing plastic tubing as necessary for various blood processing operations. The blood processing system 100 typically includes an uninterruptible power supply (UPS) 128 for maintaining electrical power to the 12-Volt power supply, the process controller 120 components, and other components in the event of a primary power loss.

Figure 3:
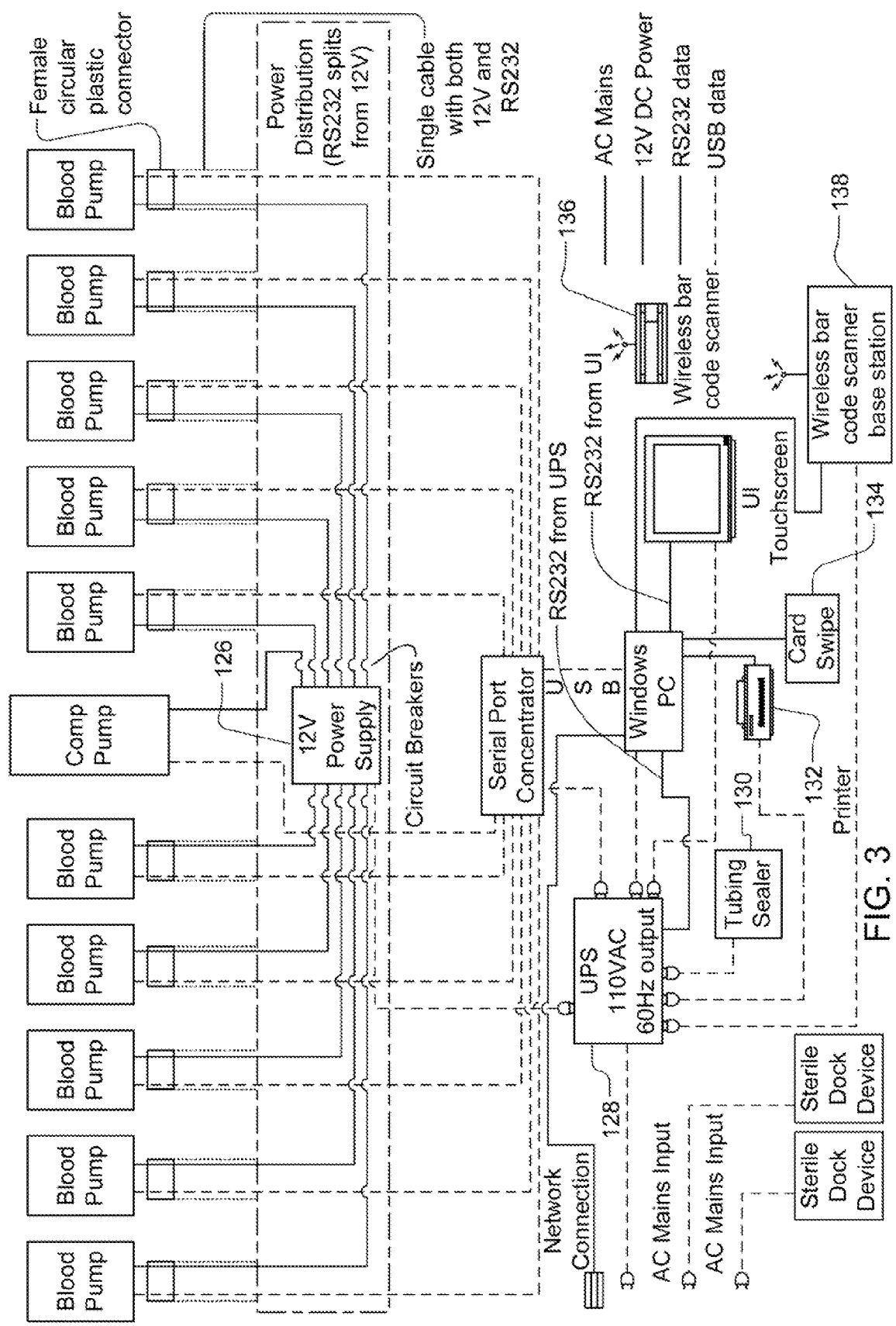
FIG. 3 shows an exemplary wiring diagram for another embodiment of the blood processing system shown in FIG. 1.

FIG. 3 shows an exemplary wiring diagram for another embodiment of the blood processing system 100. The blood processing system 100 may include a printer in communication with the process controller for printing out reports. The blood processing system 100 may include a card reader 134 in communication with the process controller for card-based operator identification. The blood processing system 100 may include a wireless bar code scanner base station 138 in communication with the process controller for receiving bar code information scanned using a wireless bar code scanner 136. Bar codes are typically used to track the various solution containers and the pumps on which those containers were processed.

The process controller 120 coordinates the actions of the compounder pump 102, the blood pumps 104, and the operator throughout the various mixing operations. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations.

Figure 4:
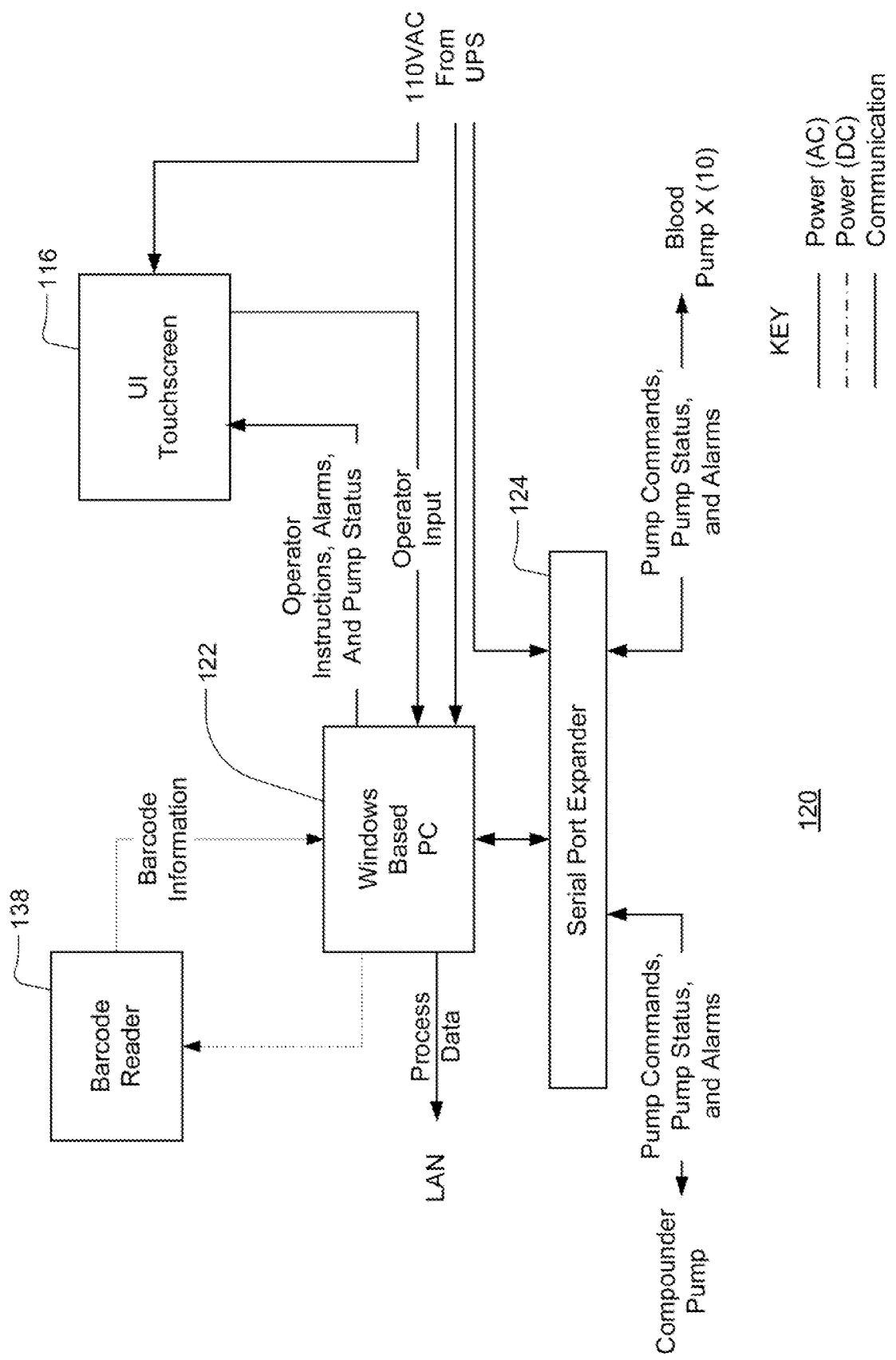
FIG. 4 is a block diagram showing additional details of the process controller in accordance with an embodiment of the present invention.

FIG. 4 is a block diagram showing additional details of the process controller 120 in accordance with an embodiment of the present invention. The computer 122 communicates with the various pumps through the serial port expander 124, including sending commands to the pumps and receiving status and alarms from the pumps. The computer 122 interacts with the operator through the user interface 116, including providing instructions, status information, and alarms to the operator and receiving operator inputs. The computer 122 receives barcode information from the barcode reader 138.

In an exemplary embodiment of the present invention, the process controller 120 coordinates blood processing for an entire bank of five blood pumps 104 at a time. Specifically, the process controller 120 ensures that there is a sufficient quantity of working solution for operating five blood pumps 104, and coordinates preparation of a batch of working solution if there is an insufficient quantity of working solution. The process controller 120 then coordinates operation of a bank of blood pumps 104 for mixing working solution with RBCC from a respective RBCC bag 106. The process controller is described in greater detail below.

Each of the pumps preferably employs disposable pump cassettes that are operated pneumatically. The pump cassette acts as an interface between the liquids being pumped and the pump unit itself so that no liquids come into direct contact with the pump unit. A compounder disposable set includes a single pump cassette coupled through a vial cap to a working solution bag, and is used to pump buffer solution from a buffer solution container through a vial of anti-pathogen compound to the working solution bag. An exemplary compounder disposable set is described in Application D84. A blood disposables set includes five pump cassettes connected to a single working solution inlet tube and to a respective incubation solution bag. The five pump cassettes are installed respectively in the five blood pumps 104 of a bank of blood pumps 104, and are used for mixing working solution with RBCC from a respective RBCC bag 106. An exemplary blood disposables set is described in Application D85.

Figure 5:
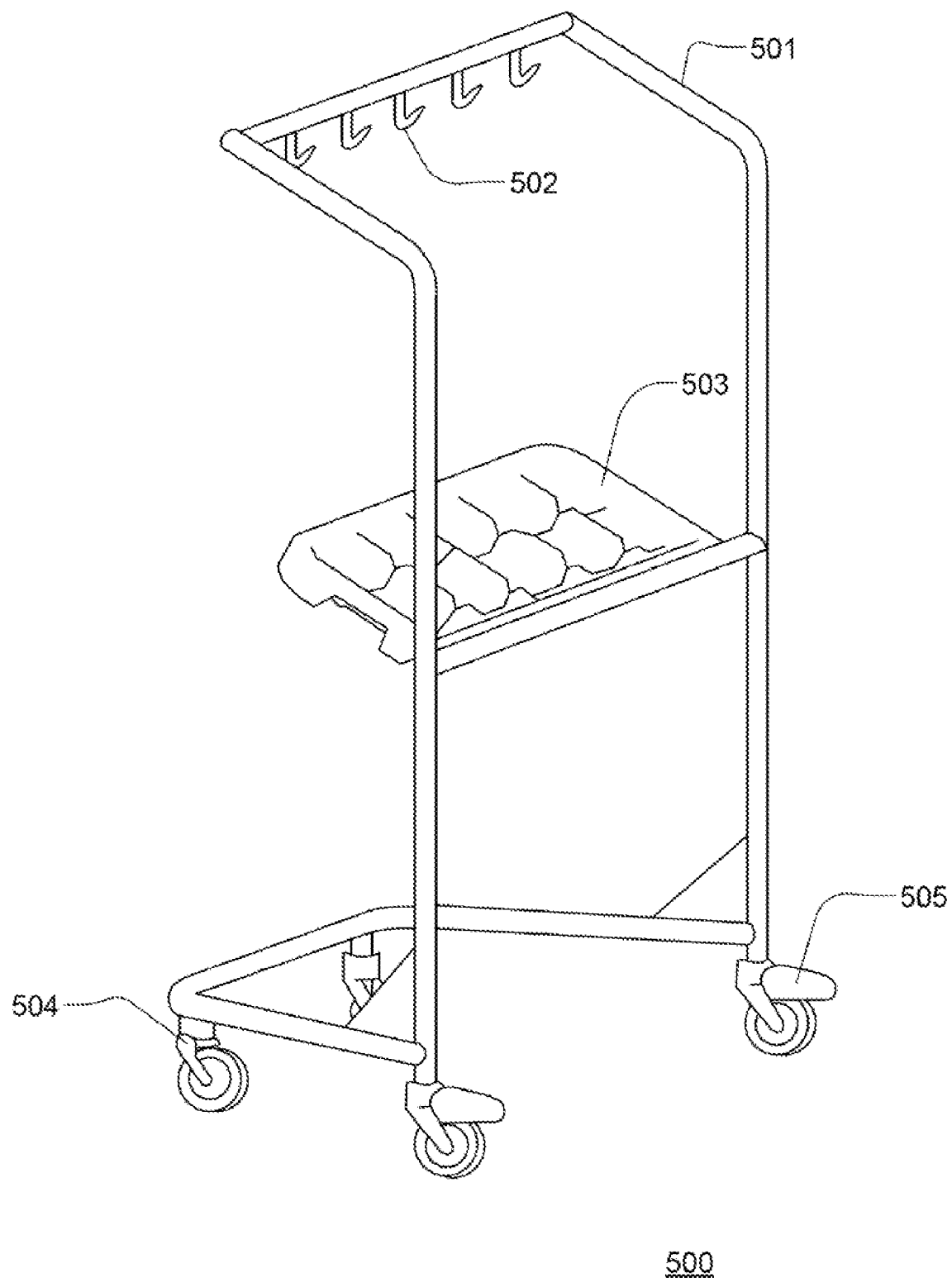
FIG. 5 shows an exemplary management rack in accordance with an embodiment of the present invention.

In order to facilitate blood processing, a portable management rack is typically used to prepare and hold the blood disposables set for use in a bank of blood pumps 104. FIG. 5 shows an exemplary management rack 500 in accordance with an embodiment of the present invention. The management rack 500 typically includes a tubular frame 501 supporting five RBC bag hooks 501 for hanging five RBCC bags 106 and a removable tray 502 having five compartments for holding the five pump cassettes and five incubation bags, respectively, of the blood disposables set. The management rack 500 also includes a pair of casters 504 and a pair of locking casters 505 situated at the base of the frame 501.

In order to prepare for a blood processing cycle, five RBCC bags 106 are hung on the hooks 502, and a blood disposables set is placed in the tray 503. The five RBCC bags 106 are connected respectively to the five pump cassettes using a sterile docking device. This is typically done at a preparation or staging area away from the actual blood processing workstation.

For actual blood processing operations, the management rack is maneuvered in front of a bank of five blood pumps 104, and the locking casters 505 are locked in order to hold the rack 500 in place. The working solution inlet tube of the blood disposables set is connected to the working solution bag using a sterile docking device 114 at the blood processing workstation. The five pump cassettes are loaded respectively into the five blood pumps 104, leaving the incubation bags in the tray 503.

Figure 6:
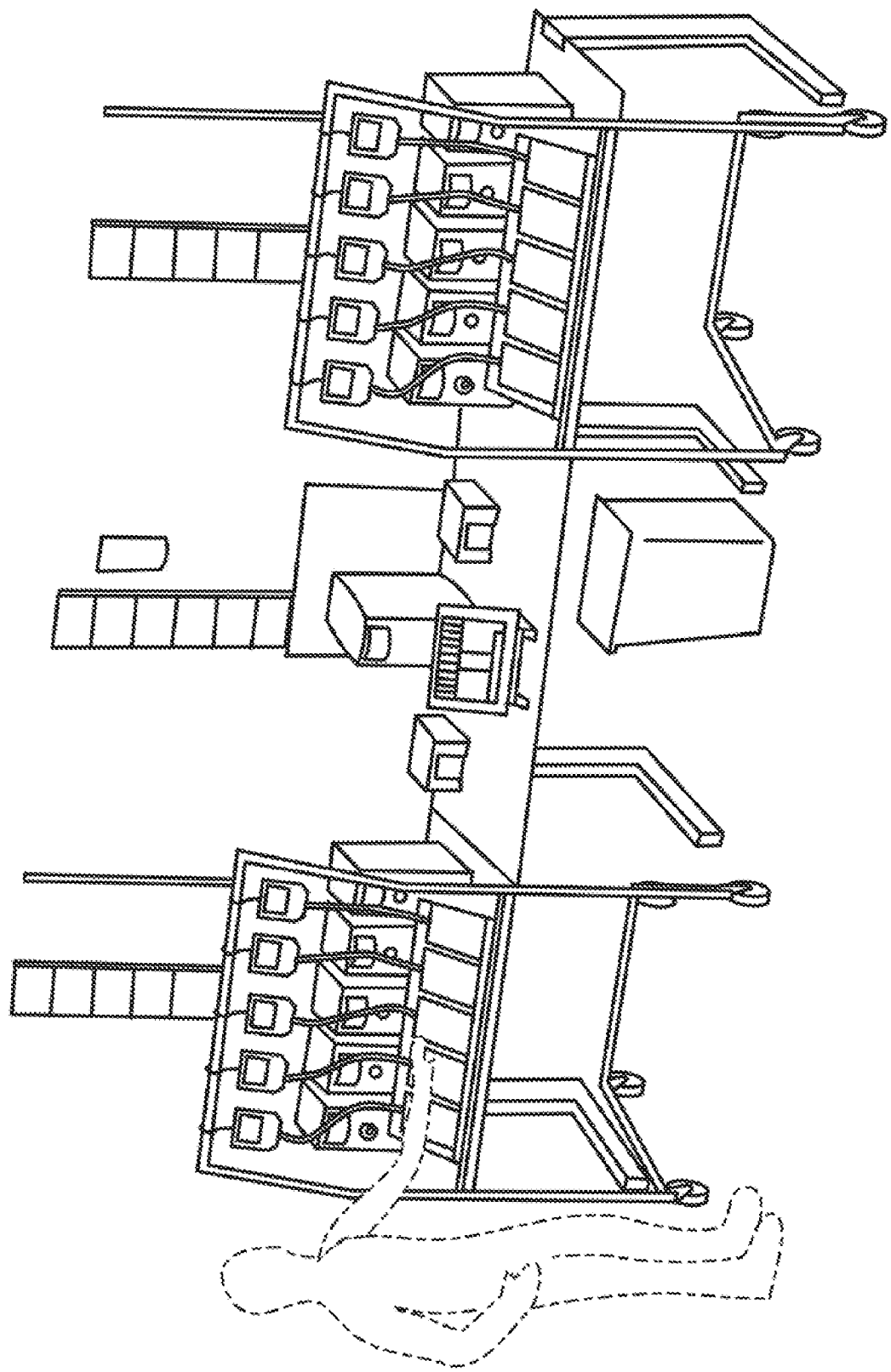
FIG. 6 shows a representation of a blood processing workstation with management racks situated in front of each bank of blood pumps in accordance with an embodiment of the present invention.

FIG. 6 shows a representation of a blood processing workstation with management racks situated in front of each bank of blood pumps in accordance with an embodiment of the present invention. The management racks are typically designed roll up to a table holding the bank of blood pumps, with the portion of the frame 501 holding the casters 504 rolling under the table so as not to interfere with operation of the blood pumps. The locking casters 505 remain easily accessible to the operator. The top portion of the frame 501 is typically bent slightly for stability of the management rack 500 as well as for positioning the RBCC bags 106 closer to the blood pumps and out of the way of the operator.

After blood processing operations are complete for a bank of blood pumps, the incubation bags are sealed and separated from the pump cassettes. The management rack 500 can then be wheeled to an incubation or staging area for unloading of the incubation bags. In a typical embodiment of the invention, the entire tray 503 is removed from the rack 500, and the incubation bags remain in the tray 503 during incubation. The trays may be designed to stack with the incubation bags in their respective compartments. Among other things, this stacking reduces the amount of space needed for incubation. The rack 500 is recycled by removing all remaining disposables and installing a new tray 503.

The various components used in the blood processing system are designed specifically to work in certain proximities to one another. For example, it is desirable for the working solution lines between the working solution container and the pump cassettes in each bank of five blood pumps to be relatively short so that the pump cassettes can be efficiently primed and the lines do not contain an excessive amount of residual working solution after blood processing operations are complete. Therefore, the blood pumps 104 in each bank of blood pumps are typically situated in close proximity to one another (e.g., side-by-side), the compounder 102 is typically located between and in close proximity to both banks of blood pumps, and the blood disposables set is designed so that the working solution lines are not excessively long. The sterile docks 114 are typically located on either side of the compounder 102 to facilitate joining the working solution line between the working solution bag and the blood disposables set.

In certain embodiments of the present invention, specialized tables are used to hold the various components of the blood processing workstation. The tables are designed to allow different workstation configurations to be formed using different combinations and orientations of the tables. In an exemplary embodiment of the invention, a workstation is formed from three different tables, specifically a trapezoidal shaped center table and two types of end tables that are essentially mirror images of one another. A single workstation can be formed in a linear (horizontal) configuration or a corner (L-shaped) by merely orienting the end tables differently. Multiple workstations can be combined to form more complex workstation configurations.

FIGS. 7A-7F show the workstation tables and various workstation configurations in accordance with various embodiments of the present invention. FIG. 7A shows a linear (horizontal) workstation configuration including a center table 701 flanked by two end tables 702 and 703. FIG. 7B shows a corner (L-shaped) workstation configuration in which the end tables 702 and 703 are essentially reversed from the linear (horizontal) configuration. FIG. 7C shows a configuration of four corner (L-shaped) workstations. FIG. 7D shows a configuration of two corner (L-shaped) workstations. FIG. 7E shows a configuration of two linear (horizontal) workstations. FIG. 7F shows a configuration of three corner (L-shaped) workstations.

Figure 8:
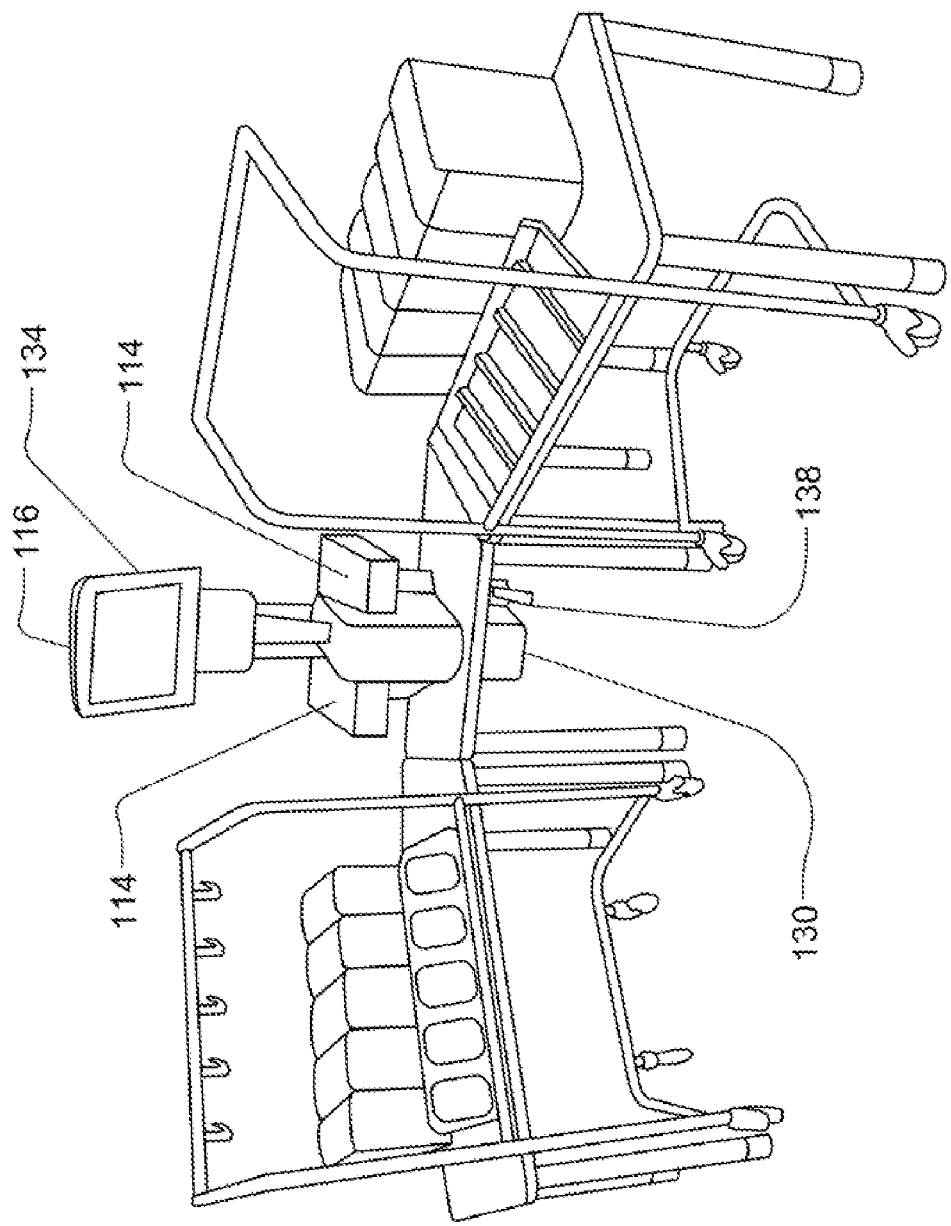
FIG. 8 shows an exemplary blood processing workstation using specialized tables in accordance with an embodiment of the present invention.

FIG. 8 shows an exemplary blood processing workstation using specialized tables in accordance with an embodiment of the present invention. The center table 701 is preferably used to support the compounder 102, the process controller 120 with user interface 116, the sterile docks 114, the bar code reader 138, and card swipe 134. Each of the end tables 702 and 703 is preferably used to support a bank of five blood pumps. In this configuration, all of the components are easily accessible to the operator.

Each workstation can be run very efficiently using two people, one to work the staging area preparing the management racks and handling the resulting incubation solutions, and the other to operate the pumps to prepare working solution and incubation solutions. The staging operator prepares management racks by hanging five RBCC bags, placing the incubation bags and pump cassettes respectively in the tray compartments, and connecting each RBCC bag to a corresponding pump cassette. The staging operator wheels the management rack to a workstation operator, who controls compounding and blood process operations. The staging operator can prepare another management rack while the workstation operator is coordinating blood process operations using the previous management rack. When a blood processing cycle is complete, the workstation operator seals the incubation bags and provides the management rack with incubation bags to the staging operator.

Process Controller

As described above, the process controller 120 coordinates the actions of the compounder pump 102, the blood pumps 104, and the operator throughout the various mixing operations. The process controller 120 initiates high level embedded commands within the pumps to move and mix the fluids. The process controller 120 instructs the operator through the setup and teardown of each process through the user interface 116. The user interface 116 is also used to inform the operator of any anomalies that may occur during mixing operations. The process controller 120 preferably coordinates blood processing for an entire bank of five blood pumps 104 at a time.

More specifically, the process controller 120 is the primary interface between the operator and the workstation. The process controller 120 interacts with the operator through the user interface in order to provide information to the operator and received inputs from the operator. The process controller 120 interacts with the pumps to send control commands to the pumps and receive status and alarm information from the pumps. The process controller 120 also receives inputs from the bar code reader and the swipe card reader.

The process controller 120 maintains various timers, including a system time and date, a running timer for the process controller, and various process timers associated with the pumps. When the process controller 120 is powered on, the operator is instructed to confirm the system time and date. The operator is required to restart the process controller if the process controller has been running continuously for more than 48 hours. The process controller 120 keeps track of the age of working solution, and prevents blood processing operations if the working solution becomes too old. Each of the pumps includes a tick counter, and the process controller compares the system clock with the tick counters to verify proper system operation.

The process controller 120 maintains an open-case file for each batch of working solution and for each unit of RBCC processed. The process controller 120 typically creates an open-case file at the time the process controller instructs the operator to load disposables into the pump. For each batch of working solution, the process controller typically maintains in the open-case file such things as a working solution batch identifier, an operator identifier, the serial number of the compounder, the working solution creation time and date (i.e., the time when the compounding operation begins), the status of the compounding operation (success or failure), and any anomalies generated during compounding. For each unit of RBCC, the process controller typically maintains in the open-case file such things as a blood bag identifier, an incubation bag identifier, the serial number of the blood pump, an operator identifier, a working solution batch identifier, the volume of RBCC processed, the volume of working solution delivered, the time and date the blood processing was completed, the status of blood processing (success or failure), and any anomalies generated during blood processing. The process controller verifies and correlates various pieces of information to ensure that the blood processing operations are valid. For example, the process controller typically verifies that all disposables were installed correctly by the operator (e.g., by scanning bar codes on the various bags and pumps, and ensuring that each blood pump is associated with an RBCC bag and an incubation bag having identical identifiers). The process controller stores the open-case files in non-volatile storage, and includes mechanisms for detecting corruption or unauthorized modification of the open-case files.

The process controller 120 also maintains a closed-case file for each batch of working solution and for each unit of RBCC processed. The process controller 120 typically creates an RBC closed-case file when the blood pump disposables are removed from the blood pump, and creates a working solution closed-case file when compounding is complete. For each batch of working solution, the process controller typically maintains in the closed-case file such things as a working solution batch identifier, an operator identifier, the serial number of the compounder, the working solution creation time and date (i.e., the time when the compounding operation begins), the status of the compounding operation (success or failure), and any anomalies generated during compounding. For each unit of RBCC, the process controller typically maintains in the closed-case file such things as a blood bag identifier, an incubation bag identifier, the serial number of the blood pump, an operator identifier, a working solution batch identifier, the volume of RBCC processed, the volume of working solution delivered, the time and date the blood processing was completed, the status of blood processing (success or failure), and any anomalies generated during blood processing. The process controller stores the closed-case files in non-volatile storage, and includes mechanisms for detecting corruption or unauthorized modification of the closed-case files.

The process controller also coordinates workstation operations during exception conditions. For example, when the blood processing system 100 is operating from the uninterruptible power supply 128 and at other appropriate times, the process controller 120 will prevent compounding and other pump operations from starting, although the pumps will generally be allowed to complete any ongoing operations. The pumps have internal logic for safely completing or terminating any ongoing operations in case the process controller fails or communication is lost with the process controller. The process controller provides an emergency stopping mechanism that the operator can invoke to stop all pumping operations (e.g., in case of a fluid leak).

As described above, the process controller 120 includes a user interface for interacting with the operator. The user interface is typically a touch screen that can be used both for displaying information to the operator and receiving inputs from the operator. The operator is typically presented with various menus for controlling workstation operations. A graphical display is also used to help focus the operator on a particular operation.

In an exemplary embodiment of the present invention, the graphical display is logically partitioned into at least two sections (windows). A graphical window is used to show a graphical representation of the status of one or more pumps, including representations of the three LEDs on the front of the pump, the physical configuration of the pump (e.g., whether disposables are loaded), and the status of the pump (e.g., currently pumping). A dialog/status window is used to display operator instructions and pump anomalies and to display the most recent pump command or operator instruction administered by the process controller. The graphical display may include action "buttons" that can be pressed or selected by the operator for performing certain functions (e.g., there may be a button for indicating that an action has been completed by the operator).

In order to focus the operator on a specific task, the process controller is generally able to control the status of the LEDs on the front of the pumps. Specifically, for each LED, the process controller can cause the LED to be turned on, turned off, or flashed at various rates. The LED states for an exemplary embodiment of the present invention are shown in Table 5 below. The process controller typically displays a representation of the pump LEDs on the graphical display so that the representation of the LEDs on the graphical display substantially match the actual status of the pump LEDs. The process controller can manipulate the LEDs on both the pumps and the graphical display to focus the operator on a specific task. For example, if multiple pumps require assistance due to a category 3 anomaly, the process controller can cause only one of those pumps to flash the red LED at a time so that the operator will focus only on one pump at a time.

Figure 9:
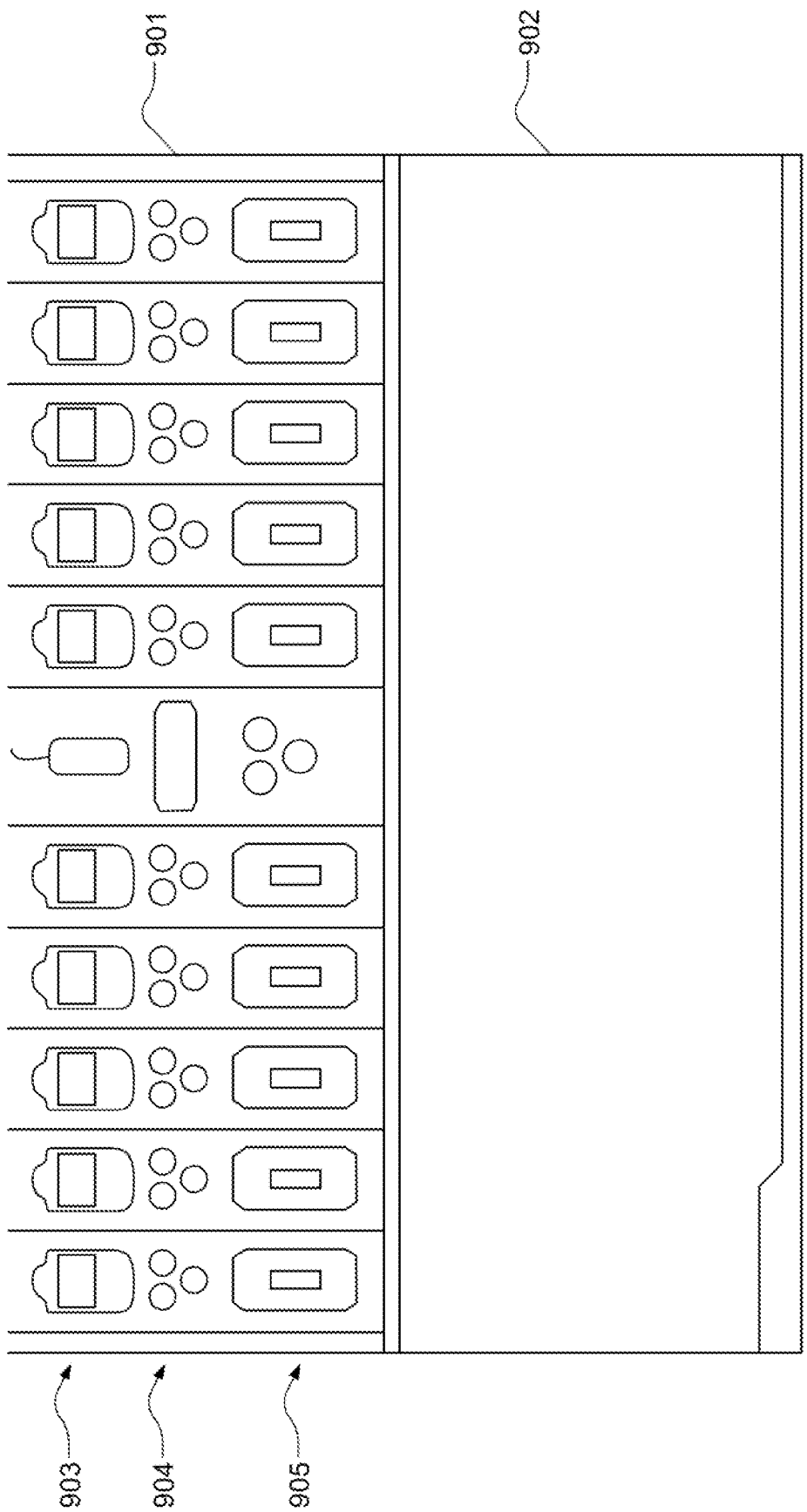
FIG. 9 shows an exemplary screenshot of a graphical display in accordance with an embodiment of the present invention.

FIG. 9 shows an exemplary screenshot of the graphical display in accordance with an embodiment of the present invention. The graphical display includes the graphical window 901 and the dialog/status window 902. In this example, the graphical window 901 shows representations of all eleven pumps. In order to help the operator correlate the information presented on the graphical display to a particular pump or pumps, the position of each pump in the graphical window 901 preferably corresponds to the physical position of the pump in the workstation, and the graphical window 901 preferably includes a representation 904 of the LEDs on each pump so that status of the LEDs displayed on the graphical display match the status of the LEDs on the pump (including color, orientation, and flash state of the LEDs). The process controller 120 can control, to some extent, the status of the LEDs on the pumps and can manipulate the LEDs to focus the operator on a specific pump. For example, the process controller 120 can ensure that only one pump has a red LED flashing so that the operator can quickly and easily identify the pump(s) that requires servicing. The graphical window 901 typically includes other icons 903 and 905 that are changed to reflect the status of the corresponding pump. For example, the icon 903 shows a blood bag, and the blood bag can be shown emptying as the corresponding blood pump processes the blood.

In order to further focus the operator on a specific task, the graphical display preferably uses a highlighting icon to highlight one or more pumps in the graphical window 901. An exemplary highlighting icon is described in Application D76. The process controller 120 uses the highlighting icon to highlight one or more pumps that require attention. The required action is typically displayed in the dialog/status window 902.

Figure 10A:
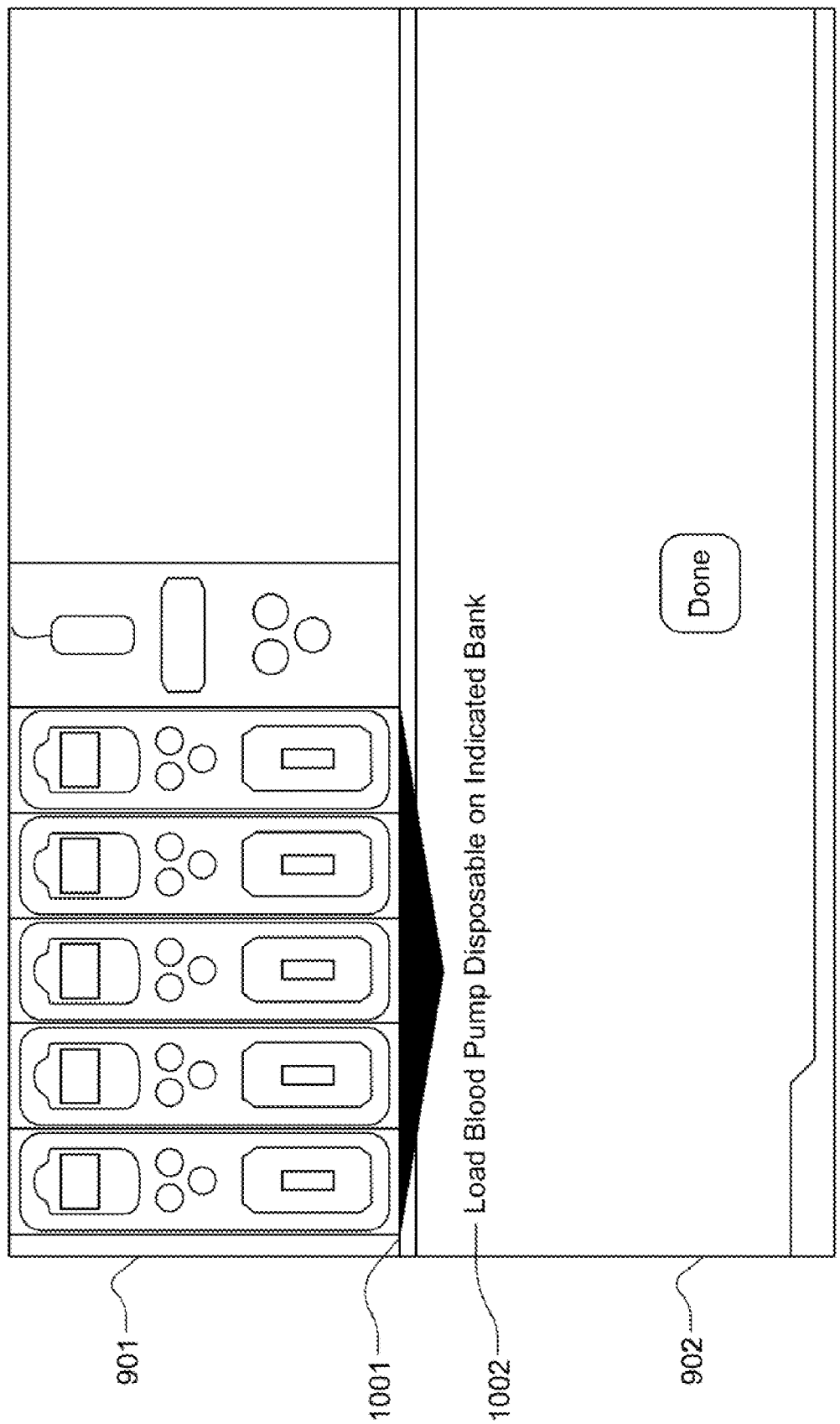
FIG. 10A shows an exemplary graphical display with a single bank of blood pumps highlighted in accordance with an embodiment of the present invention.

FIG. 10A shows an exemplary graphical display with a single bank of blood pumps highlighted in accordance with an embodiment of the present invention. The graphical display includes an icon 1001 encompassing the representations of the entire bank of blood pumps, indicating that the action 1002 displayed in the dialog/status window 902 (in this case, load blood disposables set) needs to be performed for the entire bank of blood pumps. In order to further focus the operator on the task at hand, the bank of blood pumps not requiring servicing may be removed from the graphical window 901 to reduce the chance of confusion.

Figure 10B:
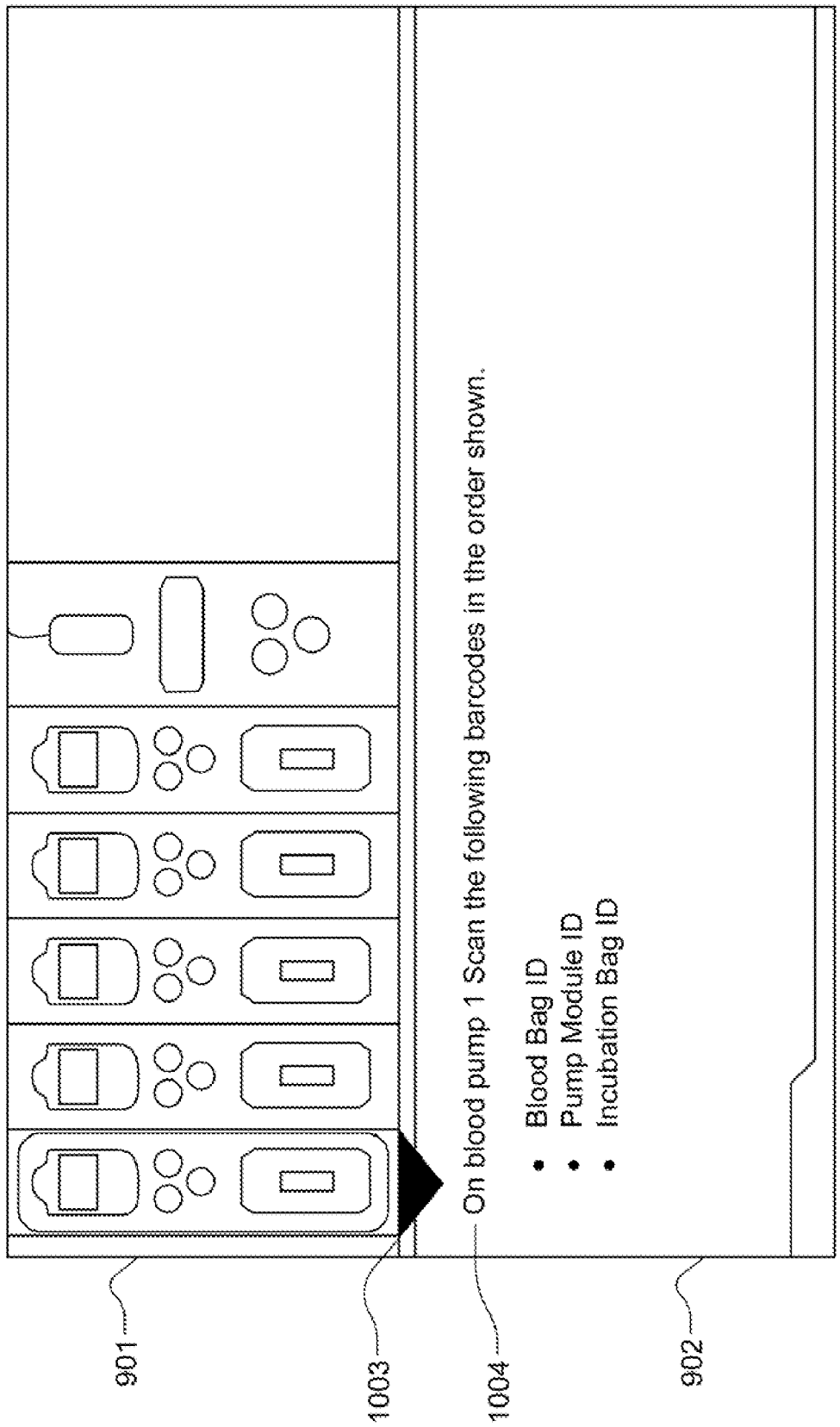
FIG. 10B shows an exemplary graphical display with a single blood pump highlighted in accordance with an embodiment of the present invention.

FIG. 10B shows an exemplary graphical display with a single blood pump highlighted in accordance with an embodiment of the present invention. The graphical display includes an icon 1002 encompassing the representations of a single blood pump, indicating that the action 1004 displayed in the dialog/status window 902 (in this case, scan bar codes) needs to be performed for that specific blood pump. Again, the bank of blood pumps not requiring servicing is removed from the graphical window 901 to reduce the chance of confusion.

Main Process

FIG. 11 is a process flow diagram showing the main process for the process controller in accordance with an embodiment of the present invention. The process begins in block 1101. When the process controller is powered on, the process controller instructs the operator to confirm the system date and time, in block 1102. If the system date and time are incorrect, then the operator is provided with a service menu, in block 1103. The service menu includes controls for the operator to shut down the workstation, perform a volume calibration test on a selected pump, adjust the system calendar and clock, print closed case files, print engineering log files, and go to the main menu. Once the system date and time are set, the process controller checks the non-volatile storage for any open-case files. If there are any open case files, this may signify that the process controller was shut down in the middle of some process, so the process controller enters an anomaly condition, in block 1105. Assuming there are no open-case files, then the process controller presents the operator with a main screen, in block 1106. FIG. 11B shows an exemplary main screen in accordance with an embodiment of the present invention. From the main screen, the operator can choose to process blood on a selected bank of blood pumps, go to a main menu, print closed-case files or engineering log files, run a volumetric calibration test, or shut down the workstation, among other things. The main menu is displayed in block 1107. In block 1108, blood processing is performed on the selected bank of blood pumps, as described below. In block 1109, the operator can choose to perform blood processing on the other bank of blood pumps, in which case the process recycles to block 1108, or tear down the compounder, in which case the process recycles to block 1106.

Figure 11A:
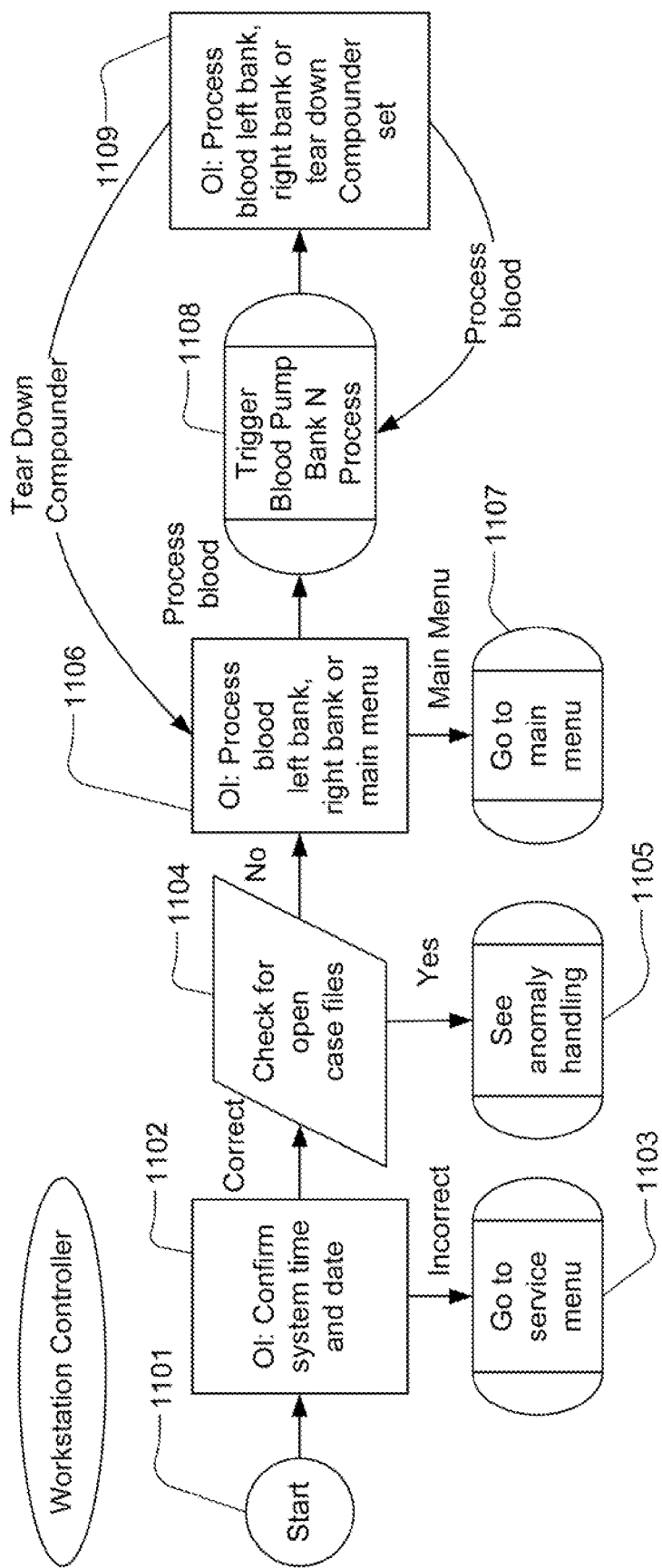
FIG. 11A is a process flow diagram showing the main process for the process controller in accordance with an embodiment of the present invention.
Figure 11B:
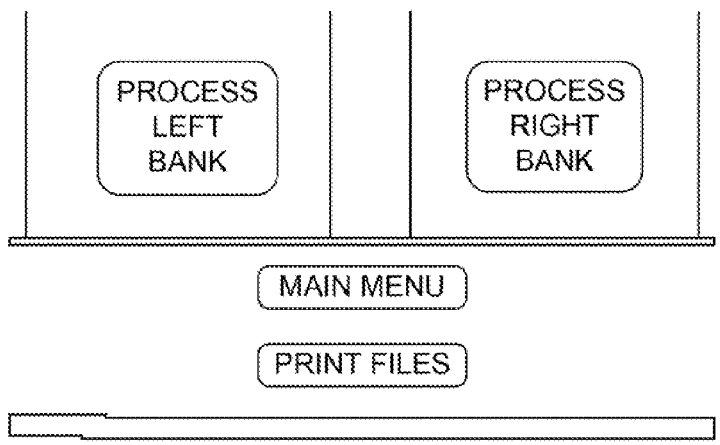
FIG. 11B shows an exemplary main screen in accordance with an embodiment of the present invention.
Figure 11C:
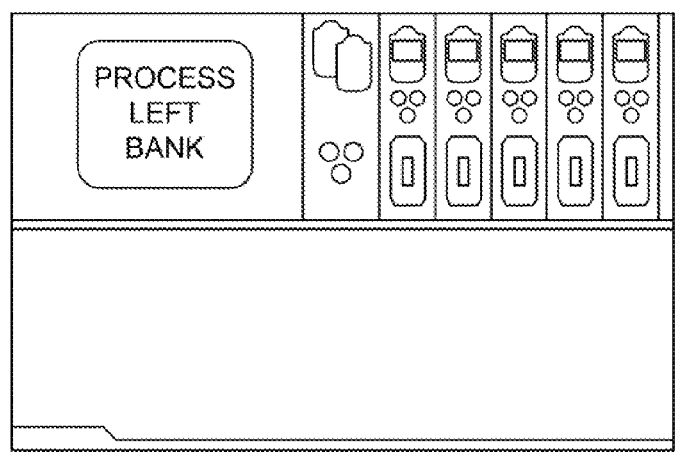
FIG. 11C shows an exemplary graphical display during processing of a bank of the blood pumps in accordance with an embodiment of the present invention.

Once a compounding or blood processing operation is in process, the process controller typically prevents the operator from accessing the main menu. FIG. 11C shows an exemplary graphical display during process of the right bank of the blood pumps, giving the operator the option of processing the left bank of blood pumps but not the option of returning to the main menu in accordance with an embodiment of the present invention.

Figure 11D:
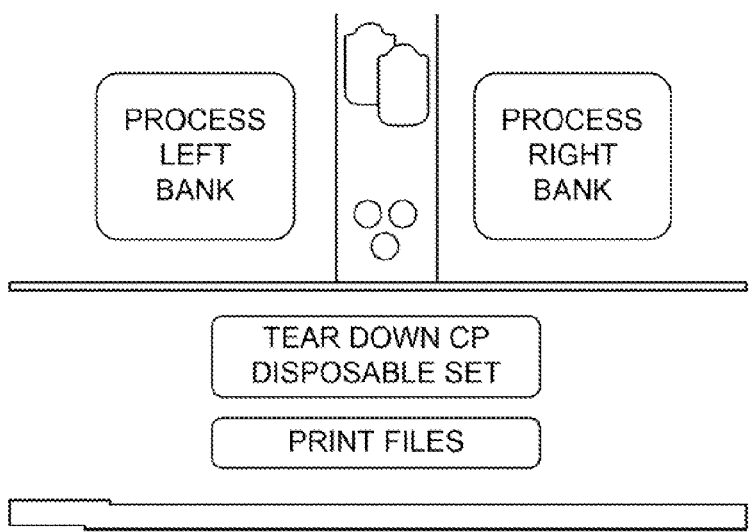
FIG. 11D shows an exemplary graphical display giving the operator the option to process blood, tear down the compounder disposables, or print closed case files in accordance with an embodiment of the present invention.

If at any time both blood pump banks become idle with no disposables loaded in them, and there is a batch of working solution ready for mixing, then the process controller gives the operator the option to process blood, tear down the compounder disposables, or print closed case files. FIG. 11D shows an exemplary graphical display giving the operator the option to process blood, tear down the compounder disposables, or print closed case files in accordance with an embodiment of the present invention.

Compounding and Blood Processing

Figure 12:
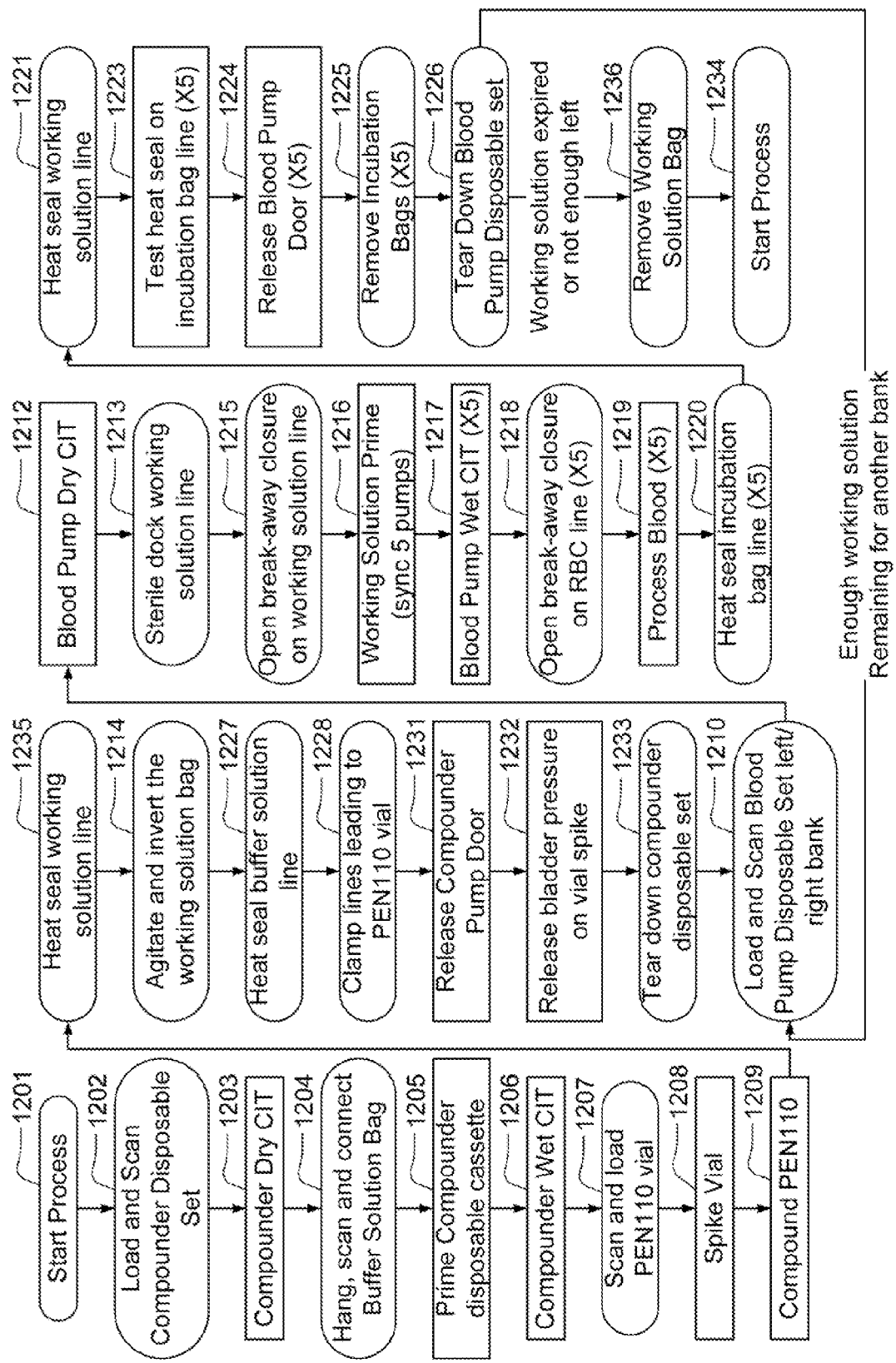
FIG. 12 shows a process flow diagram describing the compounding and blood treatment process, which is coordinated by the process controller, in accordance with an embodiment of the present invention.

FIG. 12 shows a process flow diagram describing the compounding and blood treatment process, which is coordinated by the process controller 120, in accordance with an embodiment of the present invention. Rectangular blocks indicate commands sent to the pump by the process controller 120. Rounded blocks indicate instructions sent to the operator by the process control 120.

The process starts in block 1201. In block 1202, the process controller instructs the operator to load and scan a compounder disposable set. After the compounder disposable set is loaded into the compounder, the process controller instructs the compounder to run a dry cassette integrity test (CIT) in block 1203. Assuming the dry CIT is acceptable, the process controller instructs the operator to hang, scan, and connect the buffer solution bag so that the buffer solution bag is connected to the inlet port of the pump cassette, in block 1204. The process controller then instructs the compounder to prime the compounder disposable set, in block 1205. The process controller then instructs the compounder to run a wet CIT, in block 1206. Assuming the wet CIT is acceptable, the process controller then instructs the operator to scan and load the vial assembly and spike receptacle into the vial spike assembly, in block 1207. The process controller then instructs the compounder to spike the vial, in block 1208. Once spiking is completed, the process controller instructs the compounder to perform the compounding operation, in block 1209.

As discussed above, compounding involves drawing buffer solution from the buffer solution container and pumping the buffer solution to the vial to dilute the anti-pathogen compound and pump the working solution to the working solution container. The compounder measures the volume of buffer solution pumped to the vial so that the resulting working solution will have a predetermined concentration of anti-pathogen compound, within predetermined limits. After compounding is complete, the vial will contain some amount of fluid including buffer solution and perhaps a very small amount of anti-pathogen compound.

After compounding is complete, the process controller coordinates "teardown" of the compounder for removal and disposal of the compounder disposable set from the compounder. Specifically, with reference again to FIG. 12, the process controller instructs the operator to heat seal the working solution line, in block 1235, and then agitate and invert the working solution bag, in block 1214. The process controller then instructs the operator to heat seal the buffer solution line, in block 1227. The process controller then instructs the operator to clamp the lines leading to the vial, in block 1228. The process controller then instructs the compounder to release the compounder door, in block 1231, which is accomplished by deflating the bladder in the door assembly. The process controller then instructs the compounder to release the bladder pressure on the vial spike (piston), in block 1232. The process controller then instructs the operator to remove the compounder disposables from the compounder 1233.

After compounder "teardown" is complete, the process controller coordinates the blood processing operations in which the RBCC is mixed with working solution by the blood pumps 104 in order to produce the incubation solutions. Specifically, in block 1210, the process controller 120 instructs the operator to load and scan a blood disposables set in one of the banks of blood pumps 104. The process controller 120 may instruct the operator to scan, for each blood pump, the RBCC bag 106, the blood pump 104, and the incubation bag 118. The process controller 120 stores this information so that there is a correlation between each blood pump 104 and the solutions processed and produced by it. This information can be used, for example, to identify all incubation solutions produced by a particular blood pump 104 if the blood pump 104 is found to be defective.

After the blood disposables set is loaded, the process controller 120 instructs the blood pumps 120 to perform a dry CIT, in block 1212. The dry CIT operation is described in more detail with reference to FIG. 14 below. Assuming the dry CIT is successful, the process controller 120 then instructs the operator to connect the working solution inlet tube 210 of the blood disposables set to the working solution bag 112 using the sterile dock 114, in block 1213, and open the break-away closure on the working solution inlet tube 210, in block 1215. The process controller 120 then coordinates working solution priming of the blood pumps 104, in block 1216, and then performs a wet CIT on each of the blood pumps 104, in block 1217. Assuming the wet CIT is successful, the process controller 120 instructs the operator to open the break-away closures on the RBCC inlet tubes 204, in block 1218. These break-away closures are not opened earlier in order to prevent contamination of the blood in case of a blood pump failure.

After the break-away closures are opened, the process controller 120 instructs the blood pumps 104 to mix the RBCC with the working solution to produce the incubation solutions, in block 1219. The blood mixing operation is described in more detail with reference to FIG. 17 below.

After blood mixing is complete, the process controller 120 instructs the operator to heat seal the incubation solution outlet tubes 206, in block 1220, and to heat seal the working solution distribution tubes 212, in block 1221. The process controller 120 then instructs the blood pumps 104 to test the heat seal on the incubation solution outlet tubes 206, in block 1223. Assuming the tubes are sealed, the process controller 120 instructs the blood pumps 104 to release their respective doors, in block 1224. The process controller 120 then instructs the operator to remove the incubation bags 118, in block 1225, and to tear down the blood disposables set, in block 1226.

If there is enough working solution remaining for another blood processing cycle, then the process may recycle to block 1210 to coordinate blood processing operations for another bank of blood pumps. If and when the working solution has expired or there is not enough working solution remaining for another blood processing cycle, then the process controller typically instructs the operator to remove the working solution bag, in block 1236. The process ends in block 1234.

Figure 13A:
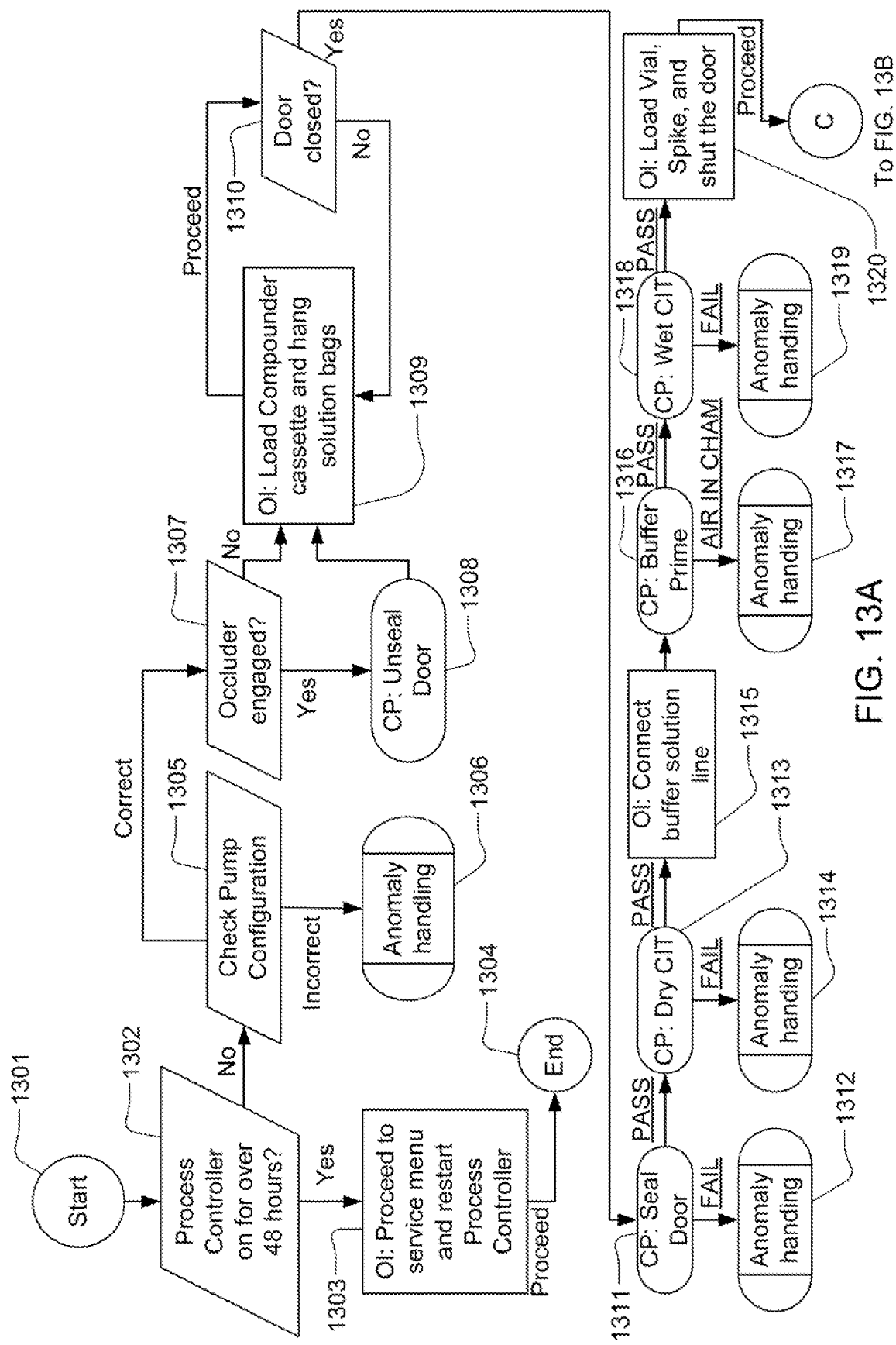
FIGS. 13A-B show a process flow diagram showing additional details of the compounding process in accordance with an embodiment of the present invention.
Figure 13B:
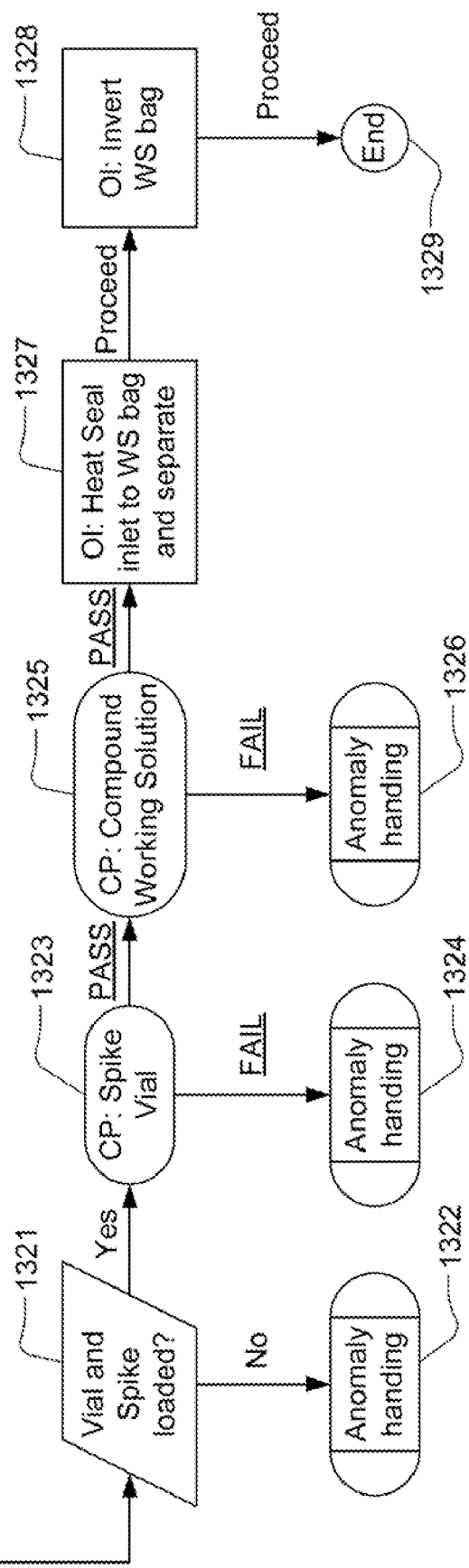

FIGS. 13A-B show a process flow diagram showing additional details of the compounding process in accordance with an embodiment of the present invention. The process begins in block 1301. The process controller first determines if it has been on for more than 48 hours, in block 1302. If so, then the process controller displays a service menu and instructs the operator to restart the process controller, in block 1303, which essentially ends this iteration of the process, in block 1304. If the process controller has not been on for more than 48 hours, then the process controller checks the compounder pump configuration, in block 1305. If the pump configuration is incorrect, then the process controller enters anomaly handling, in block 1306. If the pump configuration is correct, then the process controller checks whether the occluder is engaged, in block 1307. If the occluder is engaged, then the process controller instructs the compounder to unseal the door, in block 1308. The process controller then instructs the operator to load the compounder cassette and hang the solution bags, in block 1309. The process controller checks if the compounder door is closed, in block 1310. When the door is confirmed to be closed, the process controller instructs the compounder to seal the door, in block 1311, which is done by inflating the bladder in the door assembly. If door sealing fails, then the process controller enters anomaly handling, in block 1312. If door sealing is successful, then the process controller instructs the compounder to perform the dry CIT, in block 1313. If the dry CIT fails, then the process controller enters anomaly handling, in block 1314. If the dry CIT passes, then the process controller instructs the operator to connect the buffer solution line, in block 1315, and then instructs the compounder to prime, in block 1316. If priming fails, then the process controller enters anomaly handling, in block 1317. If priming is successful, then the process controller instructs the compounder to perform the wet CIT, in block 1318. If the wet CIT fails, then the process controller enters anomaly handling, in block 1319. If the wet CIT passes, then the process controller instructs the operator to load and lock the vial assembly and spike receptacle into the vial spike assembly, in block 1320. The process controller confirms that the vial assembly and spike receptacle are loaded and locked, in block 1321. If the vial assembly and spike receptacle cannot be loaded and locked, then the process controller enters anomaly handling, in block 1322. Upon confirmation that the vial assembly and spike receptacle are loaded and locked, the process controller instructs the compounder to perform the spiking operation, in block 1323. If spiking fails, then the process controller enters anomaly handling, in block 1324. If spiking is successful, then the process controller instructs the compounder to perform the compounding operation, in block 1325. If the compounding operation fails, then the process controller enters anomaly handling, in block 1326. Upon successful completion of the compounding operation, the process controller instructs the operator to heat seal the buffer solution line, in block 1327, and perform other operations (such as clamping the lines leading to the spike receptacle). The process controller instructs the operator to invert the working solution bag, in block 1328. The process ends in block 1329.

Figure 14A:
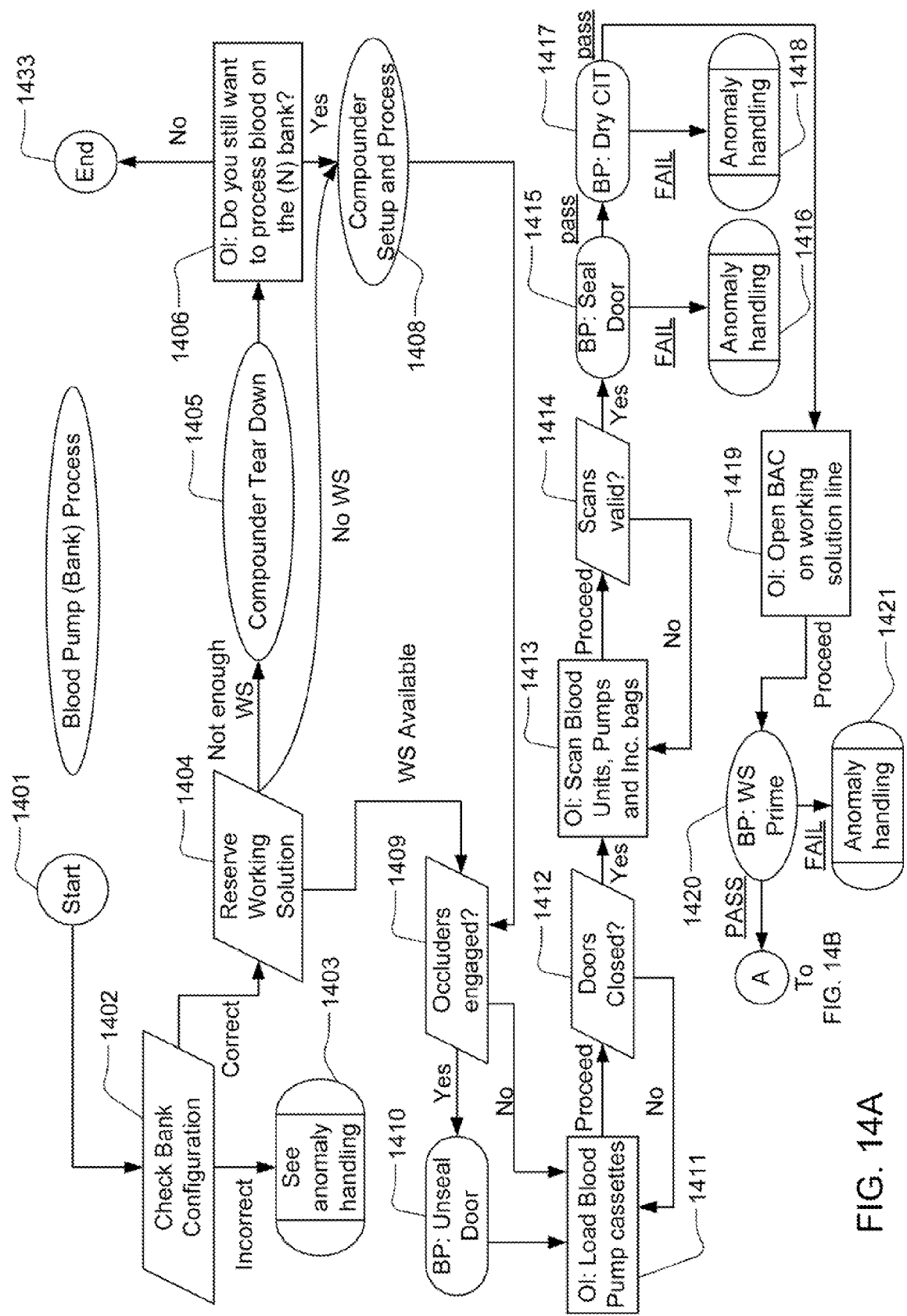
FIGS. 14A-B show a process flow diagram showing additional details of the blood processing operations in accordance with an embodiment of the present invention.
Figure 14B:
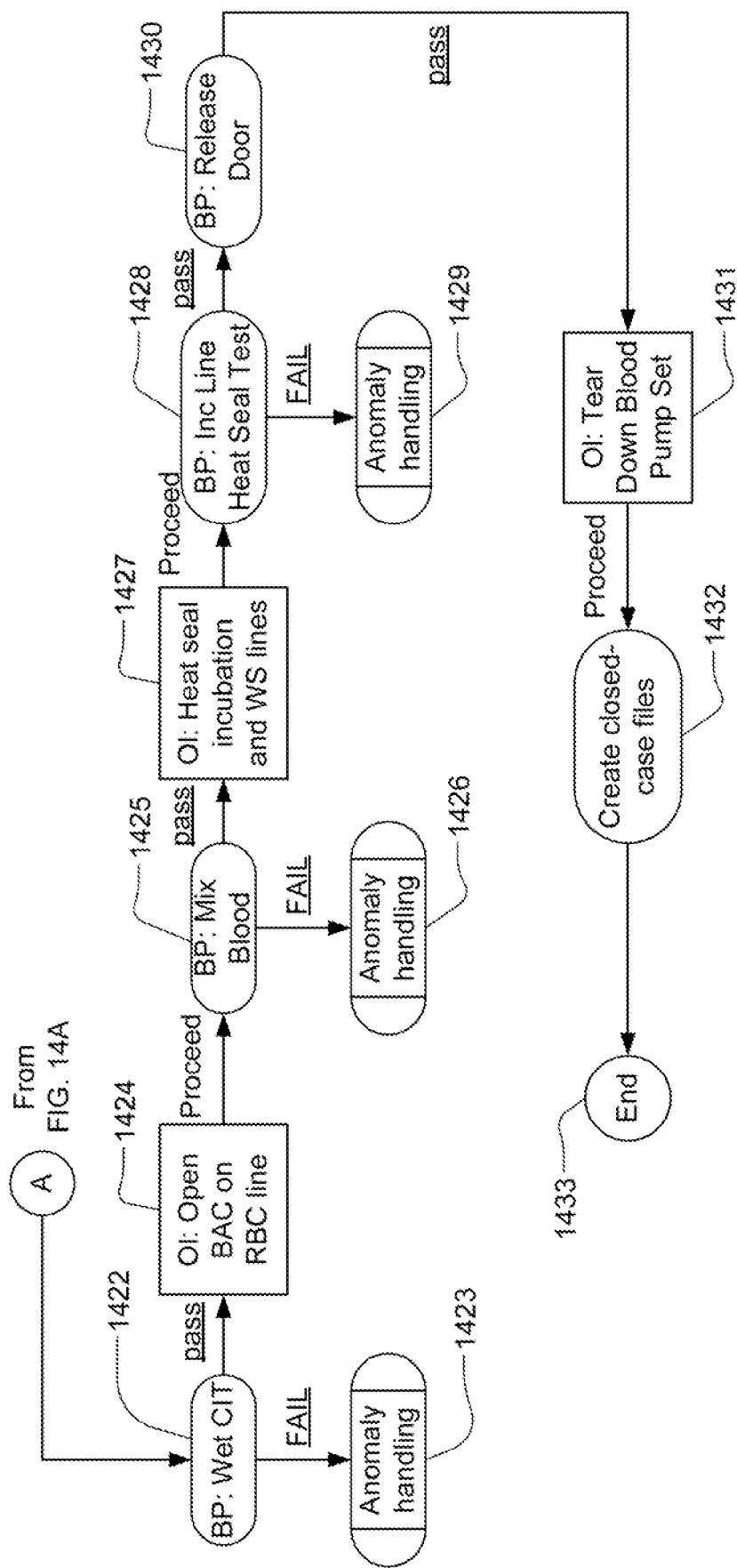

FIGS. 14A-B show a process flow diagram showing additional details of the blood processing operations in accordance with an embodiment of the present invention. The process begins in block 1401. A check is first made to confirm that the bank of blood pumps 104 is configured properly, in block 1402. This involves, among other things, confirming that there is communication between the process controller 120 and the five blood pumps 104, confirming that all five blood pumps 104 are configured to operate as blood pumps, and confirming that all five blood pumps 104 contain the correct version of embedded software. The process enters anomaly handling, in block 1403, if the bank is not configured properly.

If the bank is configured properly, then a determination is made as to whether there is a sufficient quantity of working solution and a sufficient amount of time for performing the blood processing operation, in block 1404. If there is no working solution, then the compounder setup and process operation is performed as described in Application D70, in block 1408. If there is an insufficient amount of working solution, then the compounder teardown operation is performed as described in Application D70, in block 1405, and, in block 1406, the operator is given the option to either terminate the blood processing operation, in which case the process ends in block 1433, or continue the blood processing operation, in which case the compounder setup and process operation is performed as described in Application D70, in block 1408.

If there is a sufficient quantity of working solution in block 1404, or after working solution is prepared in block 1408, the blood disposables set is loaded into the blood pumps 104. If the occluders are engaged, in block 1409, then the door is unsealed, in block 1410. Once the door is unsealed, the operator is instructed to load the blood disposables set, in block 1411, and to close the door. When the door is confirmed to be closed, in block 1414, the operator is instructed to scan the RBCC bags, blood pumps, and incubation solution bags, in block 1413. When scanning is complete, in block 1414, the blood pumps 104 are instructed to seal their respective doors, in block 1415. If a door is unable to be sealed, then the process enters anomaly handling, in block 1416, which typically includes instructing the operator to reload the pump cassette. If the door is able to be sealed, then the blood pumps 104 are instructed to perform the dry CIT, in block 1417. If the dry CIT fails, then the process enters anomaly handling, in block 1418, which typically involves instructing the operator to reload the pump cassette and running the dry CIT again. If the dry CIT passes, then the operator is instructed to connect the working solution inlet tube 210 to the working solution bag 112 using the sterile dock and to open the break-away closure on the working solution line, in block 1419. The blood pumps 104 are then instructed to perform the priming process, in block 1420. If the priming process fails, then the process enters anomaly handling, in block 1420. If priming is successful, then the blood pumps 104 are instructed to perform the wet CIT, in block 1422. If the wet CIT fails, then the process enters anomaly handling, in block 1423. If the wet CIT passes, then the operator is instructed to open the break-away closures on the RBCC inlet tubes, in block 1424. The blood pumps 104 are then instructed to mix the RBCC and the working solution to form incubation solution, in block 1425. If there is a failure during mixing, then the process enters anomaly handling, in block 1426.

Assuming blood processing is successful, the operator is instructed to heat seal the incubation and working solution lines, in block 1427. The blood units 104 are then instructed to test the seal on the incubation line, in block 1428. If the test fails, then the process enters anomaly handling, in block 1429. Assuming the incubation line is sealed, then the blood pumps 104 are instructed to release their respective doors, in block 1430, after which the operator is instructed to teardown the blood disposables set, in block 1431. A closed-case file is prepared, in block 1432. The process ends in block 1433.

Blood Pump Dry Cassette Integrity Test

The dry cassette integrity test (CIT) is used to identify air leaks in the cassette membranes prior to pumping any fluids. Identifying a cassette with a membrane hole will protect the RBCC from being contaminated by a potentially non-sterile cassette, and will reduce the potential of pumping fluid into the blood unit itself. Also, at the time of the dry CIT, an internal pressure transducer calibration check is performed in order to ensure that none of the transducers have failed or drifted out of calibration. Also during the dry CIT, the fluid valve leading to the air vent on the cassette is tested by closing the valve, pressurizing the pump chamber, and observing the pressure decay.

Blood Pump Priming

The working solution priming process operates on an entire bank of five blood pumps, where all blood pumps share a single working solution line. The working solution priming process is coordinated by the process controller 120 so as to prevent one pump from drawing in air that is being expelled by another pump, specifically by priming the operating the blood pumps symmetrically from the middle blood pump outward. Each blood pump is responsible for detecting "no flow" conditions during priming and also for detecting air in the working solution chamber of the pump cassette 202 after the priming operation is complete. The priming process uses two operations, namely a "put" operation and a "get" operation. The "put" operation involves pumping the contents of the working solution chamber of the pump cassette 202 (air and/or working solution) out through the working solution inlet 304 to the working solution bag, specifically by applying a positive pressure to the working solution chamber. The "get" operation involves drawing from the working solution inlet 304, specifically by applying a negative pressure to the working solution chamber. For convenience, the five blood pumps 104 in a bank are referred to numerically from one to five, where pump three is the middle pump of the bank, pumps two and four are the pumps adjacent to the middle pump, and pumps one and five are the outside pumps.

Figure 15:
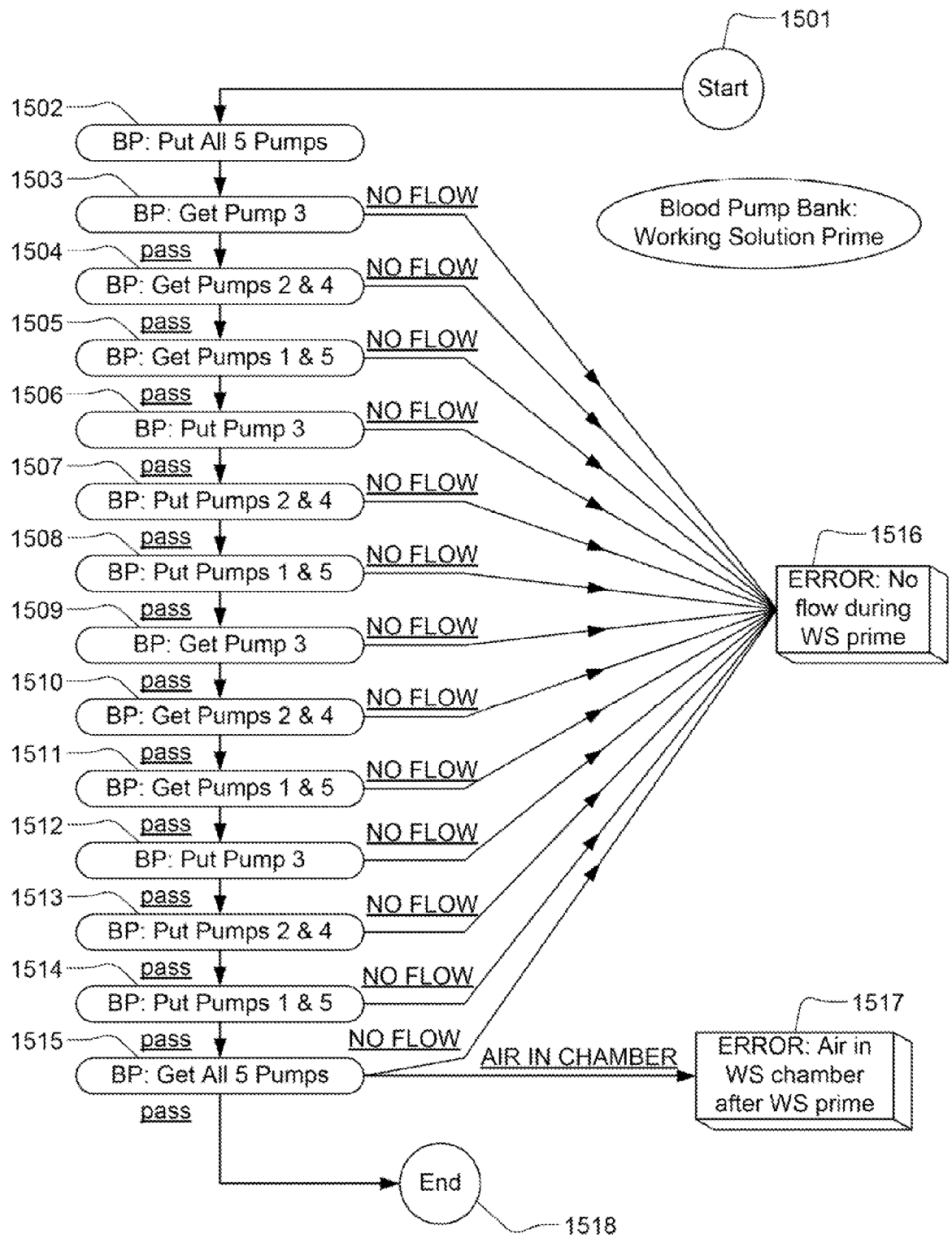
FIG. 15 shows a process flow diagram describing the blood pump working solution priming process in accordance with an embodiment of the present invention.

FIG. 15 shows a process flow diagram describing the blood pump working solution priming process in accordance with an embodiment of the present invention. The priming process begins in block 1501. In block 1502, a put operation is performed on all five blood pumps. This removes as much air as possible from the working solution chambers of the pump cassettes 102. Then, get operations are performed on the blood pumps, starting with pump three, in block 1503, then pumps two and four simultaneously, in block 1504, and then pumps one and five simultaneously, in block 1505. Then, put operations are performed on the blood pumps, starting with pump three, in block 1506, then pumps two and four simultaneously, in block 1507, and then pumps one and five simultaneously, in block 1508. Then, get operations are performed on the blood pumps, starting with pump three, in block 1509, then pumps two and four simultaneously, in block 1510, and then pumps one and five simultaneously, in block 1511. Then, put operations are performed on the blood pumps, starting with pump three, in block 1512, then pumps two and four simultaneously, in block 1513, and then pumps one and five simultaneously, in block 1514. Finally, get operations are performed on all five pumps simultaneously, in block 1518. If a blood pump detects a "no flow" condition during any of the get and put operations, an error condition is raised in block 1516, and priming is terminated. If a blood pump detects air in the working solution chamber after completion of the priming process, then an error condition is raised in block 1517. The priming process ends in block 1518.

Blood Pump Wet Cassette Integrity Test

The wet cassette integrity test (CIT) is used to identify defects within the injection-molded body of the cassette. The wet CIT involves testing the functionality of all of the fluid valves within the cassette as well as testing for "cross-talk" between the fluid paths and fluid pump chambers within the cassette. The wet CIT is performed on a partially primed cassette, after priming the working solution pump chamber, but before priming the RBC pump chamber. Therefore, a complete wet CIT is performed on the working solution pump chamber, but the RBC pump chamber is tested using air pressure and decay. Priming and wet testing of the RBC pump chamber is performed during blood mixing, as discussed below.

Compounder Pump Teardown

Figure 16:
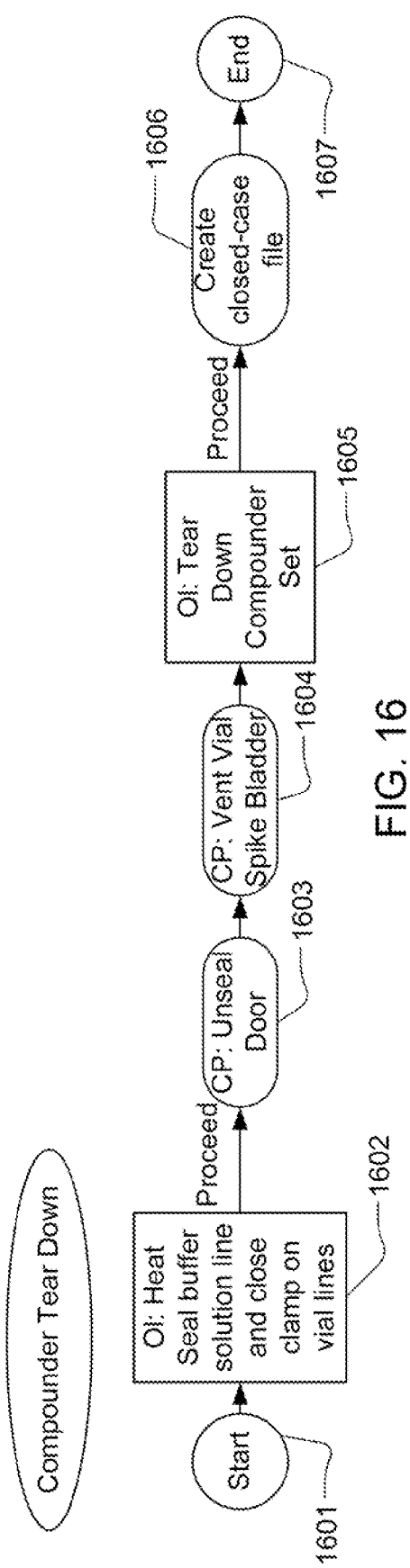
FIG. 16 shows a process flow diagram describing the process for compounder teardown in accordance with an embodiment of the present invention.

FIG. 16 shows a process flow diagram describing the process for compounder teardown in accordance with an embodiment of the present invention. The process begins in block 1601. The process controller instructs the operator to heat seal the buffer solution line and close the clamp on the vial lines, in block 1602. Upon receiving a confirmation from the operator, the process controller then instructs the compounder to unseal the door, in block 1603, and vent the vial spike bladder, in block 1604. The process controller then instructs the operator to remove the compounder disposables from the compounder, in block 1605. The process controller creates a closed-case file for the compounding cycle, in block 1606. The process ends in block 1607.

Compounder Pump Manual Teardown

During normal compounder teardown, the compounder receives commands from the process controller to release pressure against the pump door so that the door can be opened by the operator. The pressure against the door comes from both the door piston bladder and the tubing occluder. While the door piston bladder is pressurized and the tubing occluder is engaged, it is virtually impossible for the operator to open the pump door and remove the pump cassette. If communication between the process controller and the compounder is lost, then the operator will need to relieve this pressure manually in order to remove the cassette. Among other things, this involves the operator pressing the manual door release valve on the back of the pump to deflate the bladder in the door assembly. The operator may also manually retract the occluder if necessary.

Figure 17:
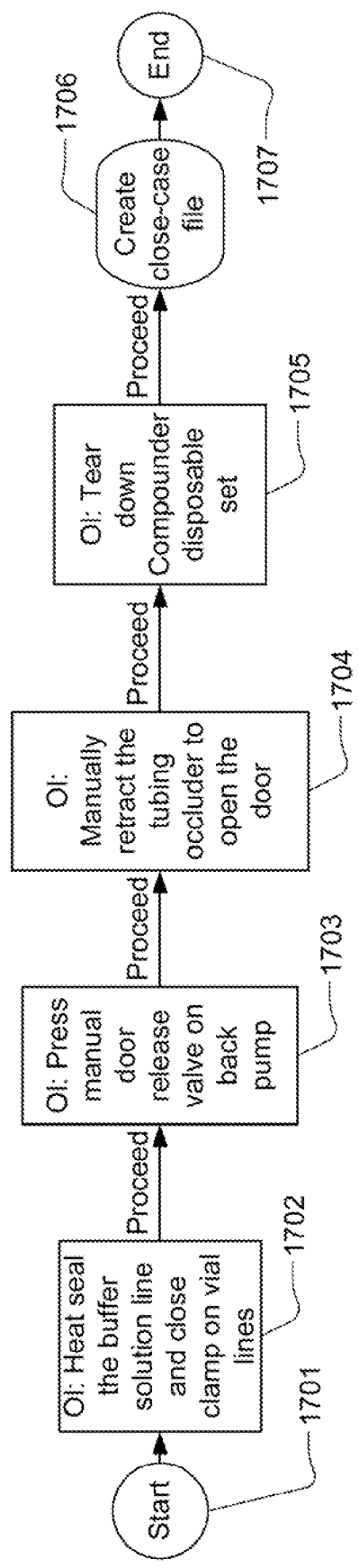
FIG. 17 shows a process flow diagram describing the process for manual compounder teardown in accordance with an embodiment of the present invention.

FIG. 17 shows a process flow diagram describing the process for manual compounder teardown in accordance with an embodiment of the present invention. The process begins in block 1701. The process controller instructs the operator to heat seal the buffer solution line and close the clamps on the lines leading to the spike receptacle, in block 1702. The process controller then instructs the operator to press the manual door release valve on the back of the pump to deflate the bladder in the door assembly, in block 1703. The process controller may then instruct the operator to manually retract the occluder if necessary to allow opening of the door, in block 1704. The process controller then instructs the operator to remove the compounder disposables, in block 1705. The process controller then creates a close-case file indicating the failure, in block 1706. The process ends in block 1707.

Blood Pump Manual Teardown

During normal blood pump teardown, the blood pump 104 receives commands from the process controller 120 to release pressure against the pump door so that the door can be opened by the operator. The pressure against the door comes from both the door piston bladder and the occluders. While the door piston bladder is pressurized and the tubing occluders are engaged, it is virtually impossible for the operator to open the pump door and remove the pump cassette. If communication between the process controller 120 and the blood pump 104 is lost, then the operator will need to relieve this pressure manually in order to remove the cassette. Among other things, this involves the operator pressing the manual door release valve on the back of the pump to deflate the bladder in the door assembly. The operator may also manually retract the occluders if necessary.

Figure 19:
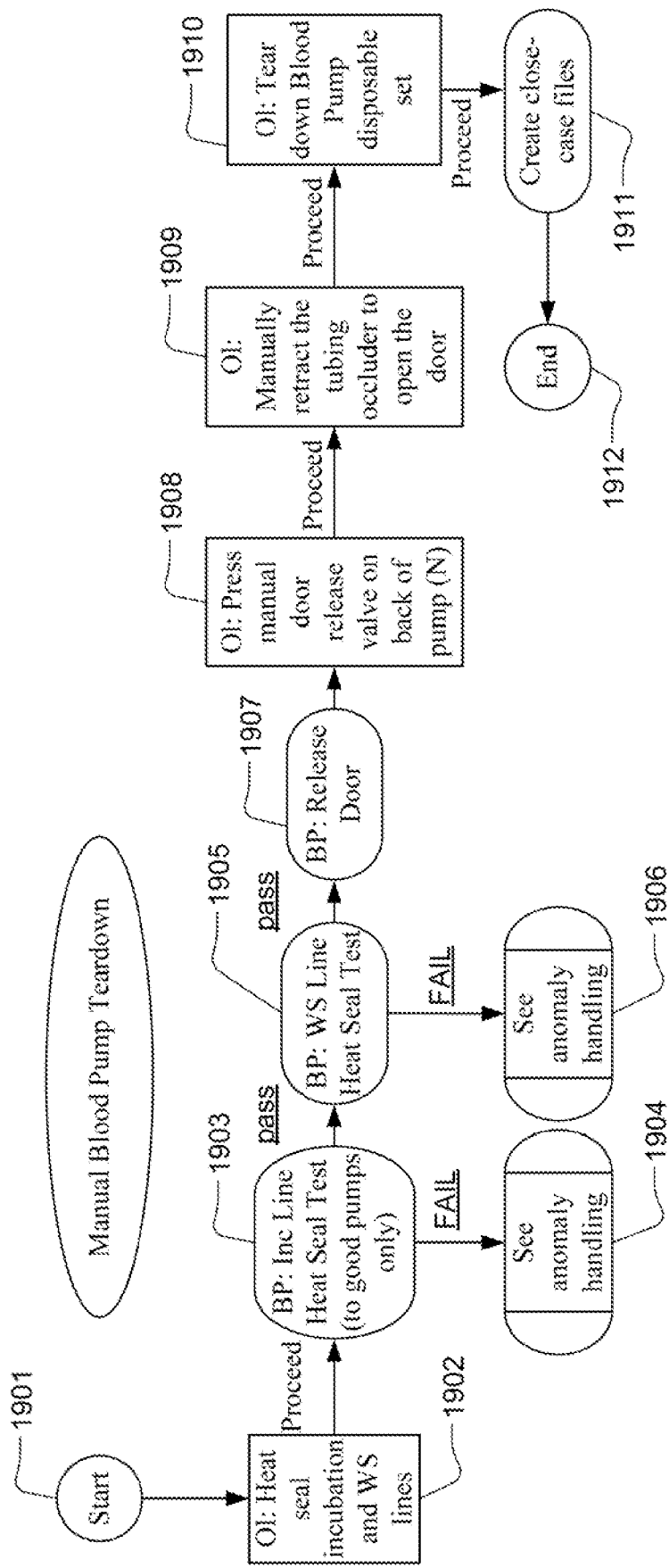
FIG. 19 shows a process flow diagram describing the process for manual blood pump teardown in accordance with an embodiment of the present invention.

FIG. 19 shows a process flow diagram describing the process for manual blood pump teardown in accordance with an embodiment of the present invention. The process starts in block 1901. The process controller first instructs the operator to heat seal the incubation and working solution lines, in block 1902. The process controller then instructs the blood pump 104 to test the heat seal of the incubation line, in block 1903. If the incubation line is not sealed, then the process controller enters anomaly handling, in block 1904. Assuming the incubation line is sealed, the process controller instructs the blood pump 104 to test the heat seal of the working solution line, in block 1905. If the working solution line is not sealed, then the process controller enters anomaly handling, in block 1906. The process controller instructs the blood pump 104 to release the door, in block 1907, and then instructs the operator to press the manual door release valve on the back of the pump to deflate the bladder in the door assembly, in block 1908. The process controller may then instruct the operator to manually retract the occluders if necessary to allow opening of the door, in block 1909. The process controller then instructs the operator to remove the blood disposables, in block 1910. The process controller then creates a close-case file indicating the failure, in block 1911. The process ends in block 1912.

Volumetric Calibration

Each pump is typically calibrated periodically to verify its ability to accurately measure volumes of pumped fluids. In exemplary embodiments of the invention, this calibration is done by running test measurements with two different test cassettes having different but known chamber volumes.

Figure 18:
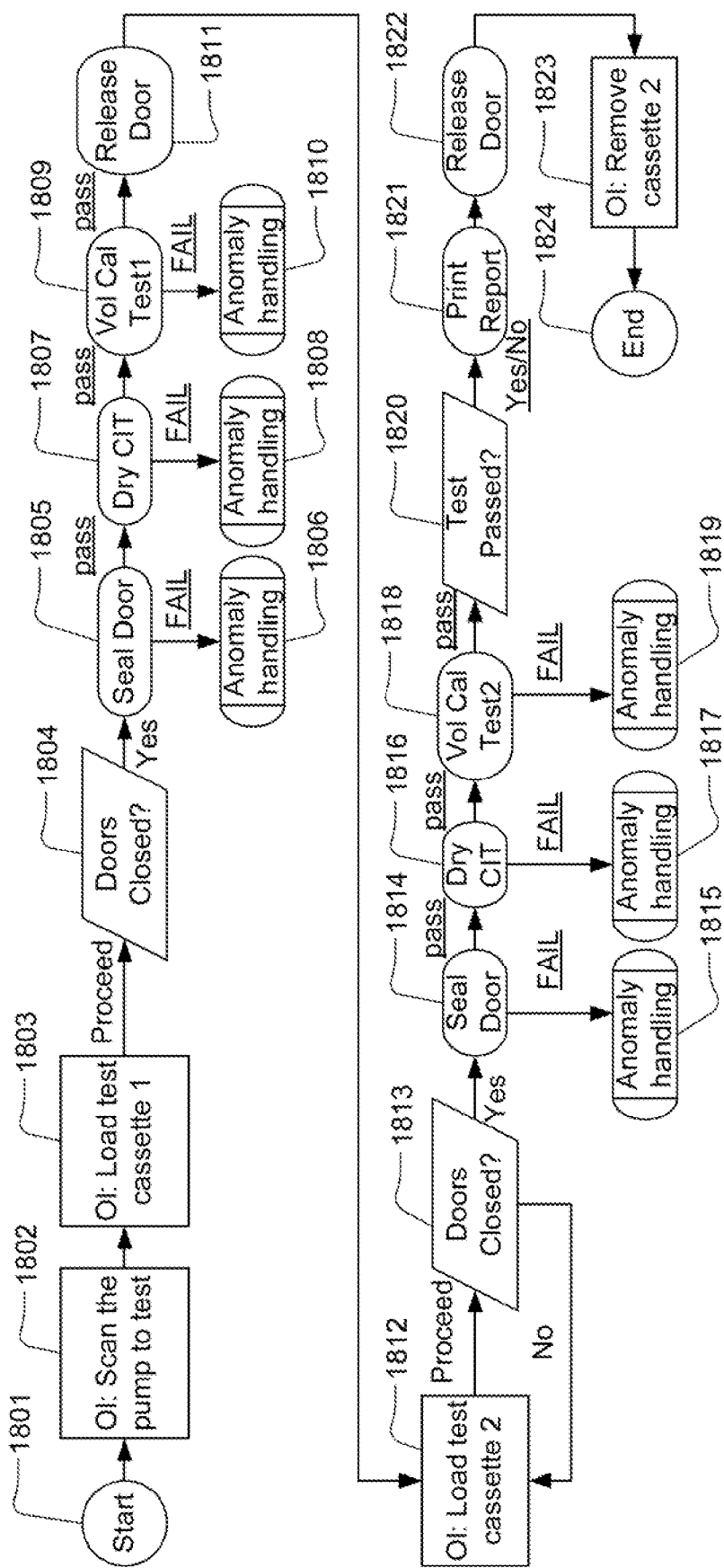
FIG. 18 shows a process flow diagram describing the volumetric calibration process in accordance with an embodiment of the present invention.

FIG. 18 shows a process flow diagram describing the volumetric calibration process in accordance with an embodiment of the present invention. The process begins in block 1801. The process controller first instructs the operator to scan a bar code on the pump in block 1802. Among other things, this identifies the pump to the process controller. The process controller then instructs the operator to load the first test cassette into the pump, in block 1803. The process controller checks for the pump door to be closed, in block 1804. Upon confirmation that the pump door is closed, the process controller instructs the pump to seal the door, in block 1805. If the door fails to seal properly, then the process controller enters anomaly handling, in block 1806. If the door seals properly, the process controller instructs the pump to run a dry CIT, in block 1807. If the dry CIT fails, then the process controller enters anomaly handling, in block 1808. If the dry CIT passes, then the process controller instructs the pump to run a first volume calibration test to measure the volume of the chambers, in block 1809. If the difference between the measured volume and the known volume of the first cassette is greater than or equal to some predetermined threshold, then the process controller enters anomaly handling, in block 1810. Otherwise, the process controller instructs the pump to release the door, in block 1811. The process controller then instructs the operator to load the second test cassette into the pump, in block 1812. The process controller checks for the pump door to be closed, in block 1813. Upon confirmation that the pump door is closed, the process controller instructs the pump to seal the door, in block 1814. If the door fails to seal properly, then the process controller enters anomaly handling, in block 1815. If the door seals properly, the process controller instructs the pump to run a dry CIT, in block 1816. If the dry CIT fails, then the process controller enters anomaly handling, in block 1817. If the dry CIT passes, then the process controller instructs the pump to run a volume calibration test to measure the volume of the chambers, in block 1818. If the difference between the measured volume and the known volume of the second cassette is greater than or equal to some predetermined threshold, then the process controller enters anomaly handling, in block 1819. Otherwise, the process controller determines whether the test passed, in block 1820, and prints a report, in block 1821. The process controller instructs the pump to release the door, in block 1822. The process controller instructs the operator to remove the second test cassette, in block 1823. The process ends in block 1824.

Anomaly Handling

In an embodiment of the present invention, there are three categories of anomaly conditions. Category 1 anomalies are fully recoverable anomalies from which it may be possible to resume normal processing if recovery is done in a timely manner. Category 2 anomalies are those from which it is not possible to resume processing blood or working solution without discarding and replacing the disposable set—if mixing has started, then the blood or working solution being processed will be lost. Category 3 anomalies indicate failures that prevent any further processing by the affected subsystem without that workstation subsystem being reset or serviced. In general, the operator is given an opportunity to cancel a process on a pump after a category 1 anomaly is detected on that pump. If a second anomaly occurs while the operator is in the process of mitigating a prior anomaly, then the operator is typically not shown the new anomaly until the process for the prior anomaly has been completed (except for certain category 3 anomalies).

Tables 1-4 describe the handling of various anomaly conditions described with reference to FIGS. 13-19 above. In Tables 1-4, the anomaly condition is shown in the lefthand column, the category is shown in the middle column, and any procedures to be taken are shown in the righthand column (with pump commands shown in bold, operator instructions enclosed within double quotation marks, and the control button provided to the operator on the graphical display enclosed within parentheses).

Table 1 shows anomaly conditions in which there is no immediate loss of working solution or RBCC.

TABLE 1

| Anomaly | Cat. | Procedure (Pump Commands/Process/"Operator Instructions", ("response button text")) |
|---|---|---|
| Seal Door Failure, Compounder (CP1-01) | 1 | "Cassette not loaded on Compounder. Load Compounder cassette or quit Compounder process." ("Load", "Quit") Unseal Compounder Door "Load Compounder cassette." ("Done") {if door not closed after operator confirms that the cassette is loaded} "Close Compounder cassette door." Seal Compounder Door |
| Barcode Data Error on Compounder Pump (CP1-02) | 1 | "Barcode data error on Compounder. Rescan the barcodes on Compounder or quit the process on the Compounder." ("Rescan", "Quit") "Scan Compounder and disposable in order shown: Two scans of working solution Run Number One scan of Compounder Pump ID" |
| Initial Dry CIT Failure, Compounder (CP1-03) | 1 | "Dry cassette test failure on Compounder. Reload cassette or quit Compounder process." ("Reload", "Quit") Unseal Compounder Door "Load the Compounder cassette." ("Done") {if door not closed after operator confirms that the cassette is loaded} "Close Compounder cassette door." Seal Compounder Door Compounder Dry CIT |
| $2^{nd}$ Dry CIT Failure, Compounder (CP2-01) | 2 | "Dry cassette test failure on Compounder. Process has failed." ("Proceed") Compounder Tear Down "Start new Compounder process or quit current process on banks." ("Start Compounder", "Quit Banks") |
| "No Flow" PEN110 Diluent Bag, Compounder (during prime) (CP1-04) | 1 | "No flow on Compounder from PEN110 Diluent bag. Check PEN110 Diluent line or quit Compounder process." ("Check Line", "Quit") "Check the PEN110 Diluent line." ("Done") Compounder Prime |
| Air in Compounder Pump Chamber (after first prime attempt) (CP1-05) | 1 | "Air detected in Compounder cassette after prime. Retry Compounder prime or quit the Compounder process." ("Retry Prime", "Quit") Compounder Prime |
| Wet CIT Failure, Compounder (CP2-02) | 2 | "Wet cassette test failure on Compounder. Process has failed." ("Proceed") Compounder Tear Down "Start new Compounder process or quit current process on banks." ("Start Compounder", "Quit Banks") |
| Vial/Vial Cap not Loaded (CP1-06) | 1 | "The PEN110 vial or vial cap is not loaded correctly on the Compounder. Reload the vial and vial cap or quit the current process on the Compounder." ("Reload", "Quit") "Load PEN110 vial and vial cap." ("Done") |
| Seal Door Failure, Blood Pump (BP1-01) | 1 | "Cassette not loaded on Blood Pump (N). Load Blood Pump cassette or quit the process on the (N) bank." ("Load", "Quit") Unseal Blood Pump Door "Load cassette on Blood Pump (N)." ("Done") {if door not closed after operator confirms that the cassette is loaded} "Close cassette door on Blood Pump (N)." Seal Blood Pump Door |

TABLE 1-continued

| Anomaly | Cat. | Procedure (Pump Commands/Process/"Operator Instructions", ("response button text") |
|---|---|---|
| Barcode Data Error on Blood Pump (BP1-02) | 1 | "Barcode data error on Blood Pump (N). Rescan the barcodes on Blood Pump (N) or quit the process on the (N) bank." ("Rescan", "Quit")<br>"On Blood Pump (N), scan the following barcodes in the order shown:<br>Blood Bag Unit ID<br>Blood Pump ID<br>Incubation Bag Unit ID" |
| Barcode Data Error on Bank (BP1-03) | 1 | "Barcode data error on the (N) bank. Rescan all of the barcodes on the (N) bank or quit the process on the (N) bank." ("Rescan", "Quit")<br>"On Blood Pump (N), scan the following barcodes in the order shown:<br>Blood Bag Unit ID<br>Blood Pump ID<br>Incubation Bag Unit ID" (repeat for all five pumps) |
| Initial Dry CIT Failure, Blood Pump (BP1-04) | 1 | "Dry cassette test failure on Blood Pump (N). Reload cassette or quit process on the (N) bank." ("Reload", "Quit")<br>Unseal Blood Pump Door<br>"Load the cassette on Blood Pump (N)." ("Done")<br>{if door not closed after operator confirms that the cassette is loaded} "Close cassette door on Blood Pump (N)."<br>Seal Blood Pump Door<br>Blood Pump Dry CIT |
| $2^{nd}$ Dry CIT Failure, Blood Pump (BP2-01) | 2 | "Dry cassette test failure on Blood Pump (N). Process on the (N) bank has failed." ("Proceed")<br>"Heat-seal and recover the RBC units on the (N) bank." ("Done")<br>Unseal Blood Pump Door (entire bank)<br>"Remove the Blood Treatment disposable set." ("Done") |
| WS about to expire prior to instructing the operator to sterile dock the common WS line (BP1-05) | 1 | "Working solution is too old. Make a new batch of working solution or quit the process on the (N) bank." ("Make Working Solution"), ("Quit")<br>Wait for Compounder to finish |
| "No Flow" Working Sol (during prime) (BP1-06) | 1 | "No flow from working solution line during prime on the (N) bank. Check break-away closure on the working solution line or quit the process on the (N) bank." ("Check Line", "Quit")<br>"Check the break-away closure on the working solution line on the (N) bank." ("Done")<br>Repeat Working Solution Prime Sequence (entire bank) |
| Air in Working Solution Pump Chamber (after 1st prime attempt) (BP1-07) | 1 | "Air detected in cassette on Blood Pump (N) after prime." ("Proceed")<br>"Check break-away closure on the working solution line or quit the process on the (N) bank." ("Check Line", "Quit")<br>"Check the break-away closure on the working solution line on the (N) bank." ("Done")<br>Repeat Working Solution Prime Sequence (entire bank) |
| Air in Working Solution Pump Chamber (after $2^{nd}$ prime attempt) (BP2-02) | 2 | "Air detected in cassette on Blood Pump (N). Process on the (N) bank has failed." ("Proceed")<br>"Triple heat-seal and recover all five RBC units on the (N) bank." ("Done")<br>"Triple heat-seal the common working solution line on the (N) bank." ("Done")<br>Unseal Blood Pump Door (entire bank)<br>"Separate the working solution line at the middle heat-seal and remove the Blood Treatment disposable set on the (N) bank." ("Done") |
| Operator chooses to quit process during a category 1 Blood Pump anomaly (Prior to Wet CIT) (BP2-03) | 2 | "Process cancelled on the (N) bank." ("Proceed")<br>"Triple heat-seal and recover all RBC units on the (N) bank." ("Done")<br>"Triple heat-seal the working solution line on the (N) bank." ("Done")<br>Unseal Blood Pump Doors<br>"Separate the working solution line at the middle heat-seal and remove Blood Treatment disposable set on the (N) bank." ("Done") |

TABLE 1-continued

| Anomaly | Cat. | Procedure (Pump Commands/Process/"Operator Instructions", ("response button text")) |
|---|---|---|
| Wet CIT Failure, Blood Pump (BP2-04) | 2 | "Wet cassette test failure on Blood Pump (N). Process on Blood Pump (N) has failed." ("Proceed") "Heat-seal and recover the RBC unit from Blood Pump (N)." ("Done") (Wait for rest of bank to finish blood process) Unseal Blood Pump Door |
| WS timer about to expire prior to instructing the operator to open break-away closures on RBC lines (BP2-05) | 2 | "Working Solution is too old. Process on the (N) bank has failed." ("Proceed") "Triple heat-seal and recover all RBC units on the (N) bank." ("Done") "Triple heat-seal the working solution line on the (N) bank." ("Done") Unseal Blood Pump Doors "Separate the working solution line at the middle heat-seal and remove the Blood Treatement disposable set on the (N) bank." ("Done") |
| "No Flow" RBC Bag (during prime stage of Mix Blood) (BP1-08) | 1 | "No flow from RBC line during prime on Blood Pump (N). Check the break away closure or quit the process on Blood Pump (N). ("Check Closure", "Quit") "Check the break away closure on the RBC line of Blood Pump (N)", ("Done") Mix Blood |
| Final Pump Chamber of RBC Out of Spec (BP1-09) | 1 | "Final chamber of RBC not recovered on Blood Pump (N)." ("Proceed") (Follow Normal Process Path) |
| Incubation Line Not Sealed (first test) (BP1-10) | 1 | "Incubation line not sealed on Blood Pump (N). Reseal the incubation line or quit the process on Blood Pump (N)." ("Reseal", "Quit") "Heat-seal incubation line on Blood Pump (N)." ("Done") Test Seal On Incubation Bag Line |

Table 2 shows anomaly conditions in which there is a loss of working solution.

TABLE 2

| Anomaly | Cat. | Procedure |
|---|---|---|
| Operator Induced Compounder Failure (During a category 1 anomaly, the operator chooses to cancel the Compounder process) (CP2-03) | 2 | "Process cancelled on the Compounder Pump." ("Proceed") Compounder Tear Down "Start new Compounder process or quit current process on banks." ("Start Compounder", "Quit Banks") |
| Vial Spike Failure (CP2-04) | 2 | "Vial spike failure. Compounder process has failed." ("Proceed") Compounder Tear Down "Start new Compounder process or quit current process on banks." ("Start Compounder", "Quit Banks") |
| "No Flow" PEN110 Vial (during Compound Working Solution) (CP2-05) | 2 | "No flow to PEN110 vial. Compounder process has failed." ("Proceed") Compounder Tear Down "Start new Compounder process or quit current process on banks." ("Start Compounder", "Quit Banks") |
| "No Flow" Pen110 Diluent line (during Compound Working Solution) (CP2-06) | 2 | "No flow from PEN110 Diluent bag during process. Compounder process has failed." ("Proceed") Compounder Tear Down "Start new Compounder process or quit current process on banks." ("Start Compounder", "Quit Banks") |
| Air in Compounder Pump Chamber (after $2^{nd}$ prime attempt or during Compound Working Solution) (CP2-07) | 2 | "Air detected in Compounder cassette. Compounder process has failed." ("Proceed") Compounder Tear Down "Start new Compounder process or quit current process on banks." ("Start Compounder", "Quit Banks") |
| Diluent to PEN110 Ratio Out of Spec (CP2-08) | 2 | "Working solution mixing error. Compounder process has failed." ("Proceed") Compounder Tear Down |

TABLE 2-continued

| Anomaly | Cat. | Procedure |
|---|---|---|
| Operator triggered emergency stop of Workstation (WS2-01) | 2 | "Start new Compounder process or quit current process on banks." ("Start Compounder", "Quit Banks") "Emergency stop button triggered." ("Proceed") "Heat-seal all fluid lines and close clamp on vial lines." ("Done") "Power up the workstation." ("Done") |
| Corrupt process data received from Compounder Pump or detected in open case file. (CP2-09) | 2 | "Corrupt process data received from Compounder. Process has failed." ("Proceed") Compounder Tear Down "Start new Compounder process or quit current process on banks." ("Start Compounder", "Quit Banks") |
| Compounder open case file detected during Workstation startup (CP2-10 | 2 | "Compounder open case file detected during startup. Process has failed." ("Proceed") Compounder Tear Down |
| Pump reset flag received from Compounder Pump during process (CP2-11) | 2 | "Compounder has been reset." ("Proceed") Compounder Tear Down "Start new Compounder process or quit current process on banks." ("Start Compounder", "Quit Banks") |

Table 3 shows anomaly conditions in which there is a loss of RBCC.

TABLE 3

| Anomaly | Cat. | Procedure |
|---|---|---|
| Operator chooses to quit process during a category 1 Blood Pump anomaly (After instructing the operator to open the closure on the RBC line) (BP2-06) | 2 | "Process cancelled on Blood Pump (N)." ("Proceed") "Triple heat-seal the RBC line on Blood Pump (N)." ("Done") (Wait for rest of bank to finish heat-seal test and tear down with them) |
| "No Flow" RBC Bag (during Mix Blood, after RBC prime stage) (BP2-07) | 2 | "No flow from RBC bag on Blood Pump (N). Process has failed." ("Proceed") "Triple heat-seal the RBC line on Blood Pump (N)." ("Done") (Wait for rest of bank to finish heat-seal test and tear down with them) |
| "No Flow" Working Sol (during Mix Blood) (BP2-08) | 2 | "No Flow from the working solution line on Blood Pump (N). Process has failed." ("Proceed") "Triple heat-seal the RBC line on Blood Pump (N)." ("Done") (Wait for rest of bank to finish heat-seal test and tear down with them) |
| "No Flow" Incubation Bag (during Mix Blood) (BP2-09) | 2 | "No flow to incubation bag on Blood Pump (N). Process has failed." ("Proceed") "Triple heat-seal the RBC line on Blood Pump (N)." ("Done") (Wait for rest of bank to finish heat-seal test and tear down with them) |
| Air in Working Solution Chamber (during Mix Blood) (BP2-10) | 2 | "Air detected in cassette on Blood Pump (N). Process has failed." ("Proceed") "Triple heat-seal the RBC line on Blood Pump (N)." ("Done") (Wait for rest of bank to finish heat-seal test and tear down with them) |
| Air in RBC Chamber (during Mix Blood) (BP2-11) | 2 | "Air detected in cassette on Blood Pump (N). Process has failed." ("Proceed") "Triple heat-seal the RBC line on Blood Pump (N)." ("Done") (Wait for rest of bank to finish heat-seal test and tear down with them) |
| Incubation Line Not Sealed (second test) (BP2-12) | 2 | "Incubation line heat-seal failure on Blood Pump (N). Process has failed." ("Proceed") (Wait for rest of bank to finish heat-seal test and tear down with them) |
| Working Solution Timer Expires While Mixing RBC (BP2-13) | 2 | "Working solution timer expired during process on Blood Pump (N)." ("Proceed") (Follow Normal Process Path) |

TABLE 3-continued

| Anomaly | Cat. | Procedure |
|---|---|---|
| Single Pump Chamber of RBC Out of Spec (BP2-14) | 2 | "Mixing error on single chamber of RBC on Blood Pump (N)." ("Proceed") (Follow Normal Process Path) |
| RBC to Working Solution Ratio Out of Spec (BP2-15) | 2 | "Mixing Error on Blood Pump (N)." ("Proceed") (Follow Normal Process Path) |
| Operator triggered emergency stop of Workstation (WS2-01) | 2 | "Emergency stop button triggered." ("Proceed") "Triple heat-seal all fluid lines and close clamp on vial lines." ("Done") "Power up Workstation." ("Done") |
| Corrupt process data received from Blood Pump or detected in open case file. (BP2-16) | 2 | "Corrupt process data from Blood Pump (N). Process has failed." ("Proceed") "Triple heat-seal RBC line on Blood Pump (N)." ("Done") (Wait for rest of bank to finish heat-seal test and tear down with them) |
| Blood Pump open case files detected during Workstation startup (BP2-17) | 2 | "Open case files detected for Blood Pump (N) during startup. Process has failed." ("Proceed") "Triple heat-seal all fluid lines on the (N) bank." ("Done") Release Door (whole bank) "Separate the working solution line at the middle heat-seal and remove Blood Treatment disposable set on the (N) bank." ("Done") |
| Pump reset flag received from Blood Pump during process (Prior to Wet CIT) (BP2-18) | 2 | "Blood Pump (N) has been reset. Process failed on the (N) bank." ("Proceed") "Triple heat-seal and recover all RBC units on the (N) bank." ("Done") "Triple heat-seal the working solution line on the (N) bank." ("Done") Unseal Blood Pump Doors "Separate the working solution line at the middle heat-seal and remove Blood Treatment disposable set on the (N) bank." ("Done") |
| Pump reset flag received from Blood Pump during process (After Wet CIT but prior to instructing the operator to open the closure on the RBC line) (BP2-19) | 2 | "Blood Pump (N) has been reset. Process has failed." ("Proceed") "Triple heat-seal and recover the RBC unit on Blood Pump (N)." ("Done") (Wait for rest of bank to finish heat-seal test and tear down with them) |
| Pump reset flag received from Blood Pump during process (After instructing the operator to open the closure on the RBC line) (BP2-20) | 2 | "Blood Pump (N) has been reset. Process has failed." ("Proceed") "Triple heat-seal the RBC line on Blood Pump (N)." ("Done") (Wait for rest of bank to finish heat-seal test and tear down with them) |

Table 4 shows anomaly conditions in which there is an immediate loss of working solution or RBCC in process on the affected pump.

TABLE 4

| Anomaly | Cat. | Procedure |
|---|---|---|
| Any detected Compounder Pump Category 3 anomaly not listed below. (CP3-01) | 3 | "Compounder Pump failure." ("Proceed") "Power cycle the Compounder Pump." ("Done") "Pump startup sequence. Please wait." |
| Any detected Blood Pump Category 3 anomaly not listed below. (BP3-01) | 3 | "Failure on Blood Pump (N)." ("Proceed") "Power cycle Blood Pump (N)." ("Done") "Pump startup sequence. Please wait." |
| Compounder Pump Not Communicating (CP3-02) | 3 | "Communication failure with Compounder Pump." ("Proceed") "Power cycle the Compounder Pump." ("Done") "Pump startup sequence. Please wait." |

TABLE 4-continued

| Anomaly | Cat. | Procedure |
| --- | --- | --- |
| Blood Pump configured as Compounder (BP3-02) | 3 | "Blood Pump (N) not configured properly." ("Proceed")<br>"Power down and remove Blood Pump (N) from the workstation." ("Done") |
| Compounder configured as Blood Pump (CP3-03) | 3 | "Compounder Pump not configured properly." ("Proceed")<br>"Power down and remove the Compounder Pump from the workstation." ("Done") |
| Blood Pump has wrong software version (BP3-03) | 3 | "Blood Pump (N) running wrong software version." ("Proceed")<br>"Power down and remove Blood Pump (N) from the workstation." ("Done") |
| Compounder Pump has wrong software version (CP3-04) | 3 | "Compounder Pump running wrong software version." ("Proceed")<br>"Power down and remove Compounder Pump from the workstation." ("Done") |
| Blood Pump Not Communicating (Prior to WS Prime complete) (BP3-04) | 3 | "Communication failure with Blood Pump (N). Process failed on the (N) bank." ("Proceed")<br>"Power cycle Blood Pump (N)." ("Done")<br>"Pump startup sequence. Please wait." |
| Blood Pump Not Communicating (After WS Prime complete, or bank not in process) (BP3-05) | 3 | "Communication failure with Blood Pump (N)." ("Proceed")<br>"Power cycle Blood Pump (N)." ("Done")<br>"Pump startup sequence. Please wait." |
| Compounder Pump not in reset after operator power cycles the pump. (CP3-05) | 3 | "Compounder Pump not reset." ("Proceed")<br>"Power cycle the Compounder Pump." ("Done")<br>"Pump startup sequence. Please wait." |
| Blood Pump not in reset after operator power cycles the pump. (BP3-06) | 3 | "Blood Pump (N) not reset." ("Proceed")<br>"Power cycle the Blood Pump (N)." ("Done")<br>"Pump startup sequence. Please wait." |
| Unable to regain communication after power-cycling failed Compounder Pump (CP3-06) | 3 | "Continuing communication failure with Compounder Pump." ("Proceed")<br>Manual Compounder Tear Down<br>"Power down and remove the Compounder pump from the workstation." ("Done") |
| Unable to regain communication after power-cycling failed Blood Pump (BP3-07) | 3 | "Continuing communication failure with Blood Pump (N)." ("Proceed")<br>If bank is in process, wait for rest of bank to finish heat-seal tests.<br>Manual Blood Pump Tear Down<br>"Power down and remove the Blood Pump from the workstation." ("Done") |
| Repeated Category 3 failure on Compounder Pump after power-cycling (CPS-07) | 3 | "Repeated failure on the Compounder Pump." ("Proceed")<br>Manual Compounder Tear Down<br>"Power down and remove the Compounder pump from the workstation." ("Done") |
| Repeated Category 3 failure on Blood Pump after power-cycling (BP3-08) | 3 | "Repeated failure on Blood Pump (N)." ("Proceed")<br>If bank is in process, wait for rest of bank to finish heat-seal tests.<br>Manual Blood Pump Tear Down<br>"Power down and remove the Blood Pump from the workstation." ("Done") |
| Volumetric Calibration Test Failure on Blood Pump (BP3-09) | 3 | "Volumetric calibration test failure on Blood Pump (N) ("Proceed")<br>Release Door<br>"Remove test cassette." ("Done")<br>"Power down and remove Blood Pump (N) from the workstation." ("Done") |
| Volumetric Calibration Test Failure on Compounder Pump (CP3-08) | 3 | "Volumetric calibration test failure on Compounder Pump ("Proceed")<br>Release Door<br>"Remove test cassette." ("Done")<br>"Power down and remove the Compounder from the workstation." ("Done") |
| Workstation running for longer than 44 hours without being restarted (WS3-01) | 3 | "Workstation uptime too long. Proceed to main menu and power down the workstation." ("Proceed") |

Upon detection of anomalies, the process controller typically executes the pump LED states shown in Table 5.

TABLE 5

| Color | Blinking | Meaning |
|---|---|---|
| Green | No | Pump is idle. Operator assistance not required. |
| Green | Slow | Pump is in process. Operator assistance not required. |
| Green | Fast | Pump is idle. Operator assistance required. |
| Yellow | No | Pump is in a category 1 or 2 anomaly. Operator assistance not required at this time. |
| Yellow | Fast | Pump is in a category 1 or 2 anomaly. Operator assistance required. |
| Red | No | Pump is in a category 3 anomaly. Operator assistance not required at this time. |
| Red | Fast | Pump is in a category 3 anomaly. Operator assistance required. |

In the exemplary embodiments described above, the primary and secondary mixing operations are performed by physically separate mixing units under the control of a separate process controller. It should be noted, however, that the present invention is in no way limited to a mixing system having separate primary and secondary mixing devices operating under control of a separate process controller. Thus, for example, primary and secondary mixing operations could be performed in a single device capable of performing both operations. Also, the process controller functions could be integrated into one of the mixing units such as, for example, the primary mixing unit (e.g., compounder pump).

It should also be noted that the flow diagrams are used herein to demonstrate various aspects of the invention, and should not be construed to limit the present invention to any particular flow or implementation. In some cases, certain process steps can be omitted or performed in a different order than shown without changing the overall results or otherwise departing from the true scope of the invention.

The present invention may be embodied in other specific forms without departing from the true scope of the invention. The described embodiments are to be considered in all respects only as illustrative and not restrictive.

What is claimed is:

1. A mixing system comprising:
a primary mixing unit configured to mix a first substance with a first liquid to produce a first solution, the first solution stored in a container;
a plurality of secondary mixing units fluidly connected to the container, each of said secondary mixing units configured to mix first solution from the container with a second substance to produce a second solution having a second predetermined concentration of first substance relative to the second substance; and
a process controller for controlling the primary and secondary mixing units, wherein the process controller determines the number of secondary mixing units fluidly connected to the container.

2. A mixing system according to claim 1, wherein the first liquid comprises a buffer solution.

3. A mixing system according to claim 1, wherein the first liquid comprises a diluting solution.

4. A mixing system according to claim 1, wherein the process controller only permits the first solution to be mixed with the second substance by the plurality of secondary mixing units before a predetermined age of the first solution.

5. A mixing system according to claim 1, wherein the process controller coordinates mixing operations of the primary and secondary mixing units.

6. A mixing system according to claim 5, wherein the process controller monitors the quantity of first solution and prevents the secondary mixing units from mixing the first solution with the second substance if there is an insufficient quantity of first solution for preparing the second solution.

7. A mixing system according to claim 6, wherein the process controller coordinates the primary mixing unit to produce a sufficient quantity of first solution for preparing the second solution by the plurality of secondary mixing units.

8. A mixing system according to claim 5, wherein the plurality of secondary mixing units are coupled to the container of first solution via a single connection to the container.

9. A mixing system according to claim 8, wherein each of the secondary mixing units requires priming with first solution prior to mixing the first solution with the second substance, and wherein the process controller coordinates priming of the plurality of secondary mixing units from the container of first solution.

10. A mixing system according to claim 9, wherein the process controller coordinates priming of the plurality of secondary mixing units symmetrically outward from the middle of the plurality of secondary mixing units.

11. A mixing system according to claim 10, comprising an odd number of secondary mixing units including a middle unit, wherein the process controller begins priming with the middle unit and continues priming outward from the middle unit with successive pairs of units.

12. A mixing system according to claim 1, further comprising: a management rack for holding a plurality of second substance containers and a plurality of second solution receptacles for use by the plurality of secondary mixing units.

13. A mixing system according to claim 12, wherein the management rack comprises a multiple compartment tray for holding the plurality of second solution receptacles.

14. A mixing system according to claim 13, wherein the multiple compartment tray is removable from the rack and is stackable with other trays while holding the plurality of second solution receptacles.

15. A mixing system according to claim 5, wherein the process controller instructs the operator to perform various tasks, and wherein the process controller focuses the operator on one task at a time.

16. A mixing system according to claim 15, wherein the process controller controls at least one visual indicator on each mixing unit for focusing the operator on one task at a time.

17. A mixing system according to claim 16, wherein the process controller provides a graphical display to the operator for focusing the operator on one task at a time, the graphical display including a representation of the at least one visual indicator of at least one mixing unit.

18. A mixing system according to claim 15, wherein the process controller provides a graphical display to the operator for focusing the operator on one task at a time, the graphical display including a representation of at least one mixing unit, the graphical display further including a highlighting icon for indicating any mixing unit associated with the task.

* * * * *